United States Patent
Albani

(10) Patent No.: US 9,707,284 B2
(45) Date of Patent: Jul. 18, 2017

(54) FORMULATIONS OF PEPTIDES AND CHLOROQUINES FOR THE TREATMENT OF PATHOGENIC IMMUNE RESPONSES IN IMMUNE MEDIATED DISEASES

(75) Inventor: Salvatore Albani, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 2198 days.

(21) Appl. No.: 12/302,685

(22) PCT Filed: Jun. 1, 2007

(86) PCT No.: PCT/US2007/013076
§ 371 (c)(1),
(2), (4) Date: Aug. 19, 2009

(87) PCT Pub. No.: WO2007/143174
PCT Pub. Date: Dec. 13, 2007

(65) Prior Publication Data
US 2010/0021485 A1    Jan. 28, 2010

Related U.S. Application Data

(60) Provisional application No. 60/810,674, filed on Jun. 1, 2006.

(51) Int. Cl.
*A61K 39/00*     (2006.01)
*A61K 38/16*     (2006.01)
*A61K 38/17*     (2006.01)

(52) U.S. Cl.
CPC ........ *A61K 39/0008* (2013.01); *A61K 38/164* (2013.01); *A61K 38/1709* (2013.01); *A61K 2039/55511* (2013.01)

(58) Field of Classification Search
None
See application file for complete search history.

(56) References Cited

U.S. PATENT DOCUMENTS 5,624,938 A    4/1997  Pernis
6,881,401 B1   4/2005  Yu et al.

FOREIGN PATENT DOCUMENTS

| CA | 2057157 | 12/1991 |
| WO | WO 02/069904 A2 | 9/2002 |
| WO | WO 03/026579 A2 | 4/2003 |
| WO | WO 03/088991 A1 | 10/2003 |
| WO | WO 2006/023029 A2 | 3/2006 |

OTHER PUBLICATIONS

Hsaio, C.-C. et al. Bone Marrow Transplant. 2002;30:905-913.*
Weinblatt, M.E. Brit. J. Rheumatol. 1996;35:403-406.*
Koffeman, E.C., et al. Arthrit. Rheum. 2009;60(11):3207-3216.*
Albani et al., "Phase II Trial of Epitope-Specific Immunotherapy in Rheumatoid Arthritis", *Arthritis and Rheumatism*, Lippincott, Philadelphia, US, 52(12):4059 (2005).
Koffeman et al., "Recent developments in immunomodulatory peptides in juvenile rheumatic diseases: from trigger to dimmer?", *Curr. Opin. Rheumatol.*, 17(5):600-605 (2005).
O'Dell et al., "Treatment of rheumatoid arthritis with methotrexate and hydroxychloroquine, methotrexate and sulfasalazine, or a combination of the three medications: results of a two-year, randomized, double-blind, placebo-controlled trial", *Arthritis Rheum.*, 46(5):1164-1170 (2002).
Siddiqi et al., "Antagonist effect of chloroquine and tumor necrosis factor on hepatic oxidative stress and antioxidant defense in normal and Plasmodium yoelii nigeriensis-infected mice", In Vivo., 16(1):67-70 (2002).
Singh et al., "Mechanism of enhancement of the antiviral action of interferon against herpes simplex virus-1 by chloroquine", *J. Interferon Cytokine Res.*, 16(9):725-731 (1996).

\* cited by examiner

*Primary Examiner* — Gerald R Ewoldt
(74) *Attorney, Agent, or Firm* — DLA Piper LLP (US)

(57) ABSTRACT

This invention concerns a pharmaceutical formulation and method for treating autoimmune disorders. The formulation and method provide for a combination therapy regimen wherein two separate substances are administered to a patient having or predisposed to having the disorder. The two components comprise at least one immunomodulatory peptide and a chloroquine derivative. The combination of the two components can be administered together or separately.

5 Claims, 9 Drawing Sheets

FIG. 1A
ACR 20
FIG. 1B
ACR 50
FIG. 1C
ACR 70
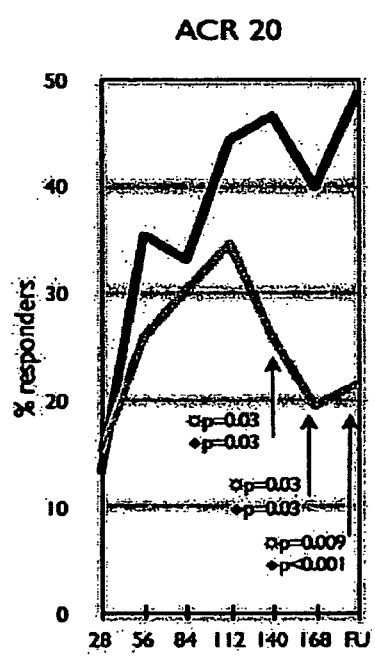
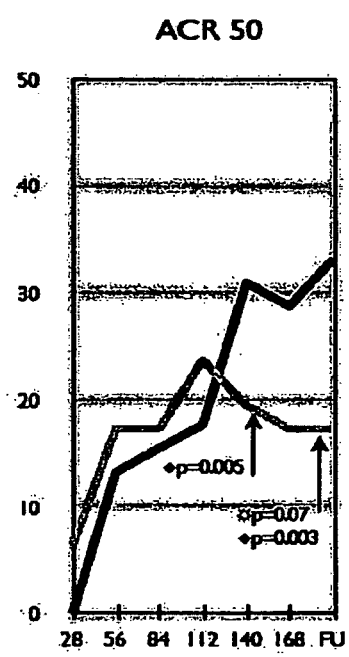
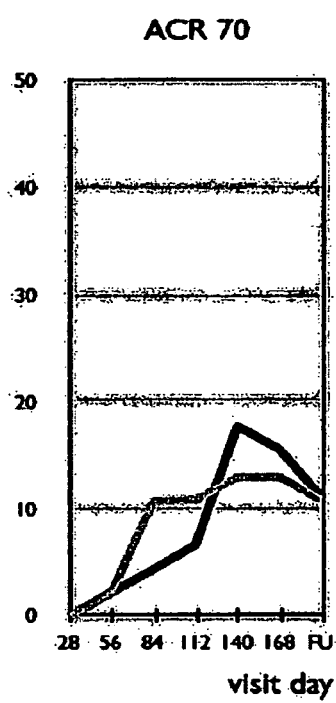

ACR 20

ACR 50

ACR 70

ACR 20

ACR 50

ACR 70

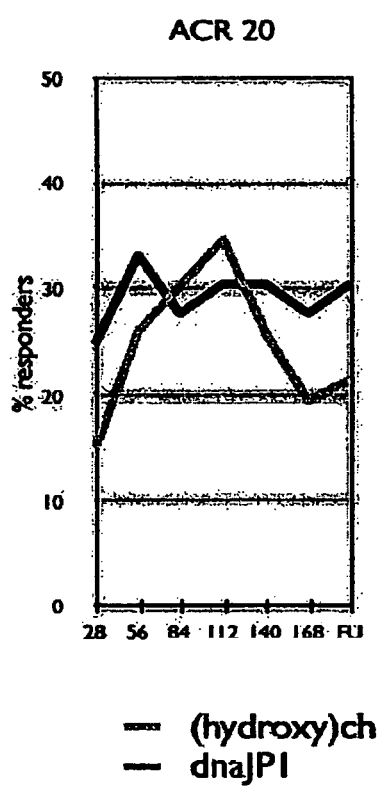
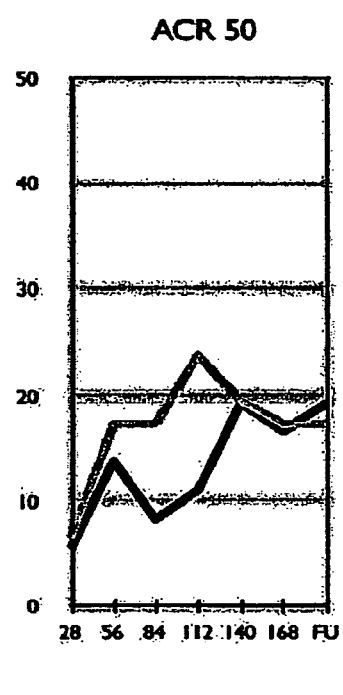
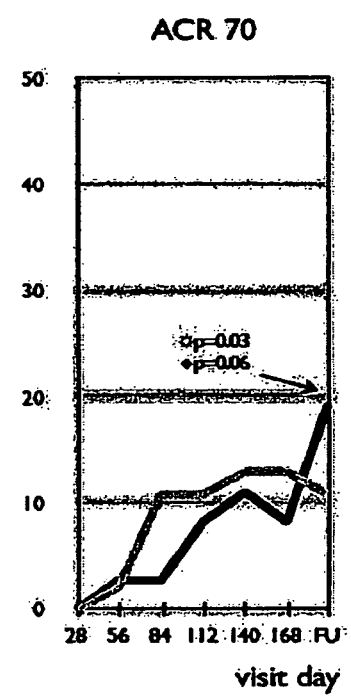
FIG. 4A ACR 20
FIG. 4B ACR 50
FIG. 4C ACR 70
— (hydroxy)chloroquine
— dnaJP1
✡CMH test   ◆GEE test

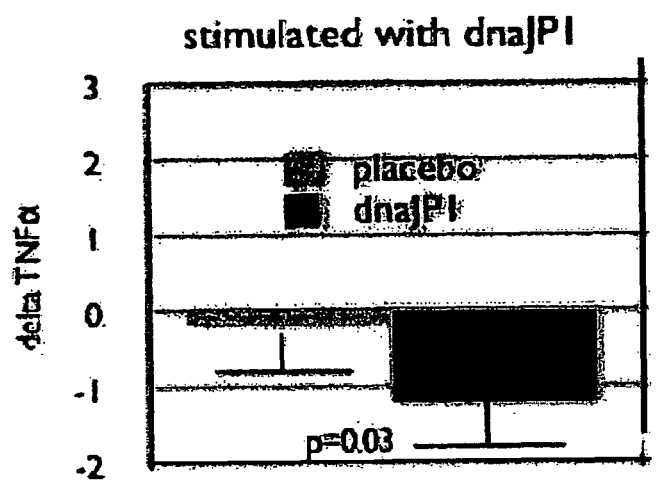
FIG. 5
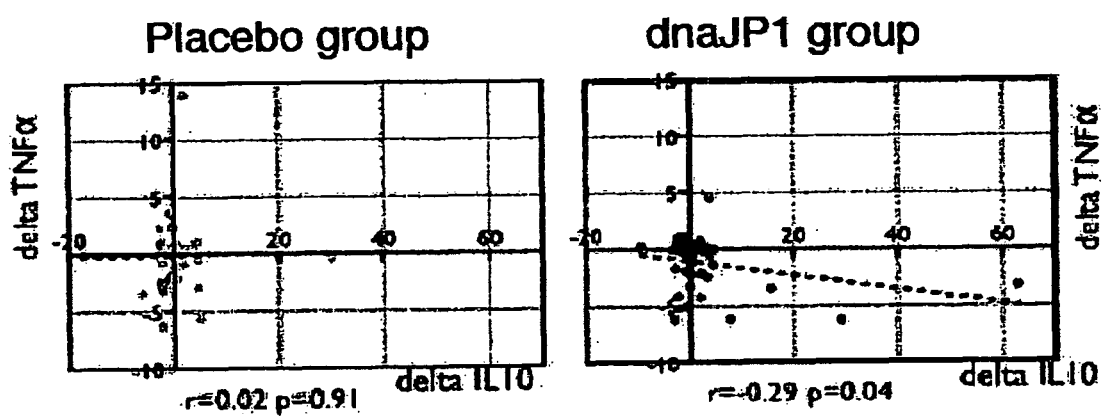
FIG. 6A
FIG. 6B

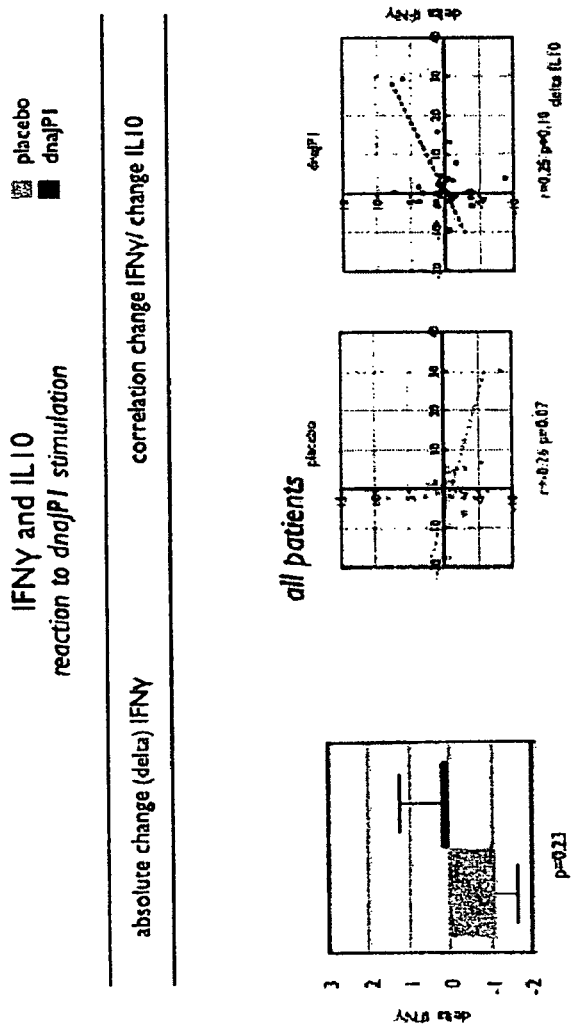

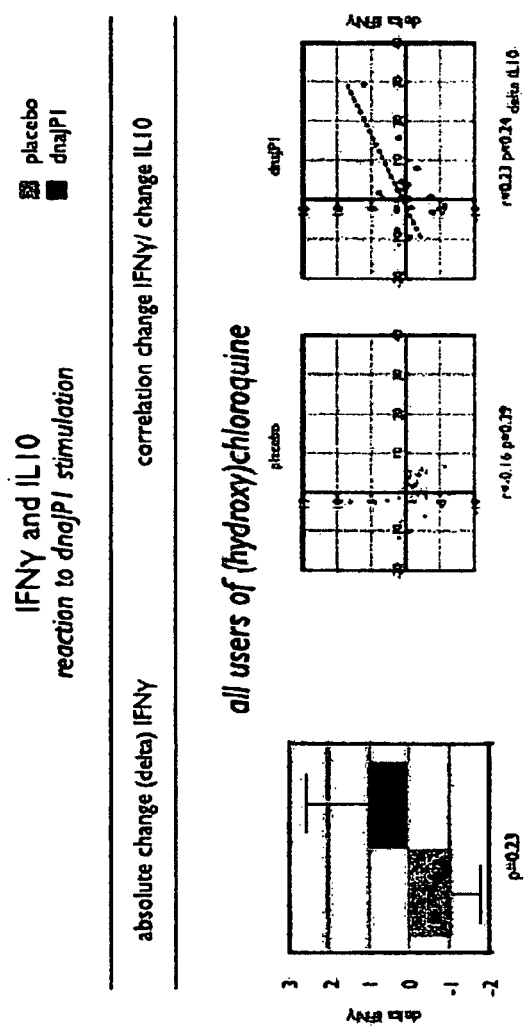

FORMULATIONS OF PEPTIDES AND CHLOROQUINES FOR THE TREATMENT OF PATHOGENIC IMMUNE RESPONSES IN IMMUNE MEDIATED DISEASES

CROSS REFERENCE TO RELATED APPLICATIONS

This application is a 35 U.S.C. §371 National Stage application of International Application No. PCT/US2007/013076 filed Jun. 1, 2007; which claims the benefit under 35 U.S.C. §119(e) to U.S. Application Ser. No. 60/810,674, filed Jun. 1, 2006. The disclosure of each of the prior applications is considered part of and is incorporated by reference in the disclosure of this application.

GRANT INFORMATION

This invention was made with government support under Grant No. NO1-AR-9-2241 awarded by the National Institutes of Health. The United States government has certain rights in this invention.

BACKGROUND OF THE INVENTION

Field of the Invention

This invention relates to immune modulation oriented therapies for treating autoimmune disorders, and more specifically, to combination treatment therapies for ameliorating autoimmune toxicity in immune-mediated diseases.

Background Information

The following description includes information that may be useful in understanding the present invention. It is not an admission that any such information is prior art, or relevant, to the presently claimed inventions, or that any publication specifically or implicitly referenced is prior art.

Recent therapies for treating rheumatoid arthritis and other human autoimmune diseases have been based on non-specific suppression of the immune system. Treatment regimens so based target inflammatory immune pathways which result in having to be concerned with balancing toxicity caused by the non-specificity with the intended perceived benefits of disease remission.

For example, with respect to rheumatoid arthritis, first generation biologic agents have included those that interfere with the inflammatory cascade by blocking one or another component, for example an inflammatory cytokine such as TNFα. Such direct biological interference with pathogenic pathways is being considered for an ever-increasing number of molecules, primarily cytokines, to replace generalized pharmacological immunosuppression for a more tailored treatment route.

Given the further understanding that recognition of self is a physiologic and necessary phenomenon, and that "quality" and "intensity" of the immune responses is regulated by complex mechanisms that ensure that recognition of self does not lead to damage, and that necessary inflammatory responses, aimed at clearing perceived "danger" such as an infection, are down regulated once "danger" is eliminated, there is a need in the art for treatment regimens which take into account the complex set of complementary and interactive pathways that contribute to the qualitative and quantitative regulation of immune responses in order to prevent tissue damage. In this context affecting the immune system towards tolerance is akin to employing a dimmer switch; i.e., rather that causing complete on/off shifting of pathways, the reactivity is lessened. Thus, further treatment regimens focused on tolerance pathways should consider this complexity in order not to bring about toxic immune reactivity.

Some tolerance pathway-focused treatment regimens, such as in therapies for rheumatoid arthritis, are not antigen specific. Data suggests that blunting, or dimming down immune responses in a non-specific fashion may lead to undesirable effects with regard to frequency and gravity of occurrence which obviously varies according to the individual therapy and regimen. Thus, a need still exists in the art for a treatment method and therapeutic formulations and compositions to advance the immune treatment arts.

SUMMARY OF THE INVENTION

The present invention relates to inflammatory autoimmune disorders, such as rheumatoid arthritis and other human autoimmune diseases and disorders and the treatment thereof comprising administration of a combination of immunomodulatory peptide(s) and a chloroquine derivative.

In one embodiment, the invention provides methods of treating autoimmune disorders by administering to a patient in need thereof a combination of a therapeutic amount of one or more immunomodulatory peptide(s) and a chloroquine derivative for ameliorating autoimmune toxicity in the patient. In one embodiment, the immunomodulatory peptide is selected from the group of sequences disclosed in Table I.

In another embodiment, the invention provides a method for treatment of inflammatory autoimmune disorders, such as rheumatoid arthritis and other human autoimmune diseases and disorders including but not limited to rheumatoid arthritis (RA), juvenile idiopathic arthritis, (JIA), psoriatic arthritis (PA), and psoriasis by mucosal administration of a combination of immunomodulatory peptide(s) and a chloroquine derivative. By immunomodulatory peptide is meant a polypeptide comprising any order of amino acids, or a mimetic peptide molecule that can bind to an MHC class II molecule and influence immune pathways in a disease relevant manner.

In another embodiment, the invention provides methods of treating RA, JIA, PA and psoriasis comprising mucosal administration of at least one immunomodulatory peptides comprising heat shock protein derived polypeptides or mimetics thereof and at least one derivative of chloroquine In another embodiment, the invention provides a pharmaceutical composition that includes a combination of at least one immunomodulatory heat shock polypeptide and at least one derivative of chloroquine. The composition may be in solid, colloidal, liquid, vapor or gas phase. In a related embodiment the formulation can further include pharmaceutically acceptable salts and/or other substances as are well known to those of ordinary skill in the arts. In a further related embodiment the formulation can comprise one formula mixture for administration to a patient in need thereof or separate formulated compositions intended to be administered separately, sequentially, or simultaneously, or any combination thereof for use in a treatment regimen for beneficial outcome to a patient.

In another embodiment, the invention comprises a treatment regimen for administering the peptide(s) and the chloroquine derivative. Generally, both peptide(s) and chloroquine can be administered together in an absorbable form to the mucosa of a patient in need thereof. Alternatively, the peptide(s) and chloroquine components can be administered separately from one another in any order also by mucosal delivery to the patient.

In another aspect, the invention provides use of peptide mimetics or peptidic derivatives and other molecular structures that mimic the molecular structure of naturally occurring heat shock protein derived polypeptide sequences and/or that possess the ability to bind MHC class II molecules and also influence the modulation of immune pathways in a disease relevant manner. As such, the invention provides methods of identifying an agent useful for treating an autoimmune disorder.

BRIEF DESCRIPTION OF THE DRAWINGS

FIGS. 1A-1C are graphs showing levels of response to treatment with immunomodulatory peptide and (hydroxyl)chloroquine. As shown in FIG. 1A recipients of dnaJP1 and HCQ according to ACR20 exhibit a surprising and unexpected apparent synergistic response. FIG. 1B shows results of ACR50 response while FIG. 1C shows ACR70 results.

FIG. 2A shows ACR20 response percentage, FIG. 2B shows results of ACR50 response while FIG. 2C shows ACR70 results.

FIG. 3A shows ACR20 response percentage, FIG. 3B shows results of ACR50 response while FIG. 3C shows ACR70 results.

FIGS. 4A-4C show results for all patients in the study receiving either dnaJP1 alone or (hydroxyl)chloroquine. FIG. 4A shows ACR20 response percentage, FIG. 4B shows results of ACR50 response while FIG. 4C shows ACR70 results.

FIG. 5 is a bar graph showing the correlation of a decrease in TNFα with dnaJP1 stimulation with little effect observed for placebo.

FIGS. 6A and 6B are plots showing shift towards increase of IL-10 following treatment. As indicated the dnaJP1 groups correlated with an increase whereas the placebo group did not.

FIGS. 7A-7C show production of IFN-γ and IL-10 by T cells from all patients treated in the study with placebo (n=79) and dnaJP1 (n=81). Results are expressed as the difference between day 168 and day 0 in the percent of CD3+ T cells producing IFN-γ (FIG. 7A). FIGS. 7B and 7C show the correlation of IL-10 production. Both IFN-γ and IL-10 increasing in the HCQ-dnaJP1 combination group at day 168.

FIGS. 8A-8C show production of IFN-γ and IL-10 in the same manner as in FIGS. 7A-7C, except that the data is for all patients receiving HCQ.

DETAILED DESCRIPTION OF THE INVENTION

Figure 2A:
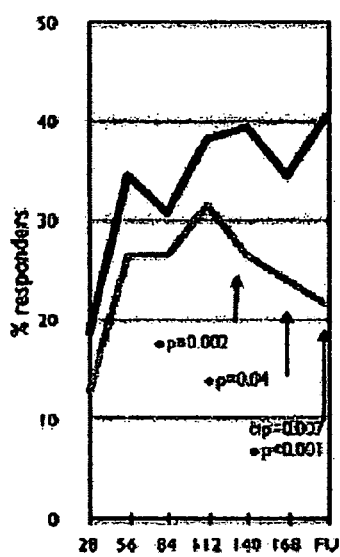
FIGS. 2A-2C show results of all patients in the study according to the same criteria as in FIG. 1, namely.

The present invention provides formulations and methods of treating a variety of autoimmune disorders, e.g., rheumatoid arthritis, juvenile idiopathic arthritis, inflammatory bowel disease, Crohn's disease, and multiple sclerosis, psoriatic arthritis, and psoriasis.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "protein" or "peptide" as used herein, refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration.

The term "cytokine" is used broadly herein to refer to soluble glycoproteins that are released by cells of the immune system and act non-enzymatically through specific receptors to regulate immune responses. As such, the term "cytokine" as used herein includes chemokines, interleukins, lymphokines, monokines, interferons, colony stimulating factors, platelet activating factors, tumor necrosis factor-alpha, and receptor associated proteins, as well as functional fragments thereof.

As used herein, the term "functional fragment" refers to a peptide or polypeptide portion of a protein that possesses the biological function or activity characteristic of the native protein. For example, a functional fragment of IFNγ or TNFα has, for example, substantially the same pro-inflammatory activity as naturally occurring or recombinantly produced IFNγ or TNFα, respectively.

The term "antibody" as used in this invention is meant to include intact molecules of polyclonal or monoclonal antibodies, as well as fragments thereof, such as Fab and F(ab')$_2$, Fv and SCA fragments which are capable of binding an epitopic determinant.

The term "subject" as used herein refers to any individual or patient to which the invention methods are performed. For example, a subject may be any one having or at risk of having cytomegalovirus infection. Generally the subject is human, although as will be appreciated by those in the art, the subject may be an animal.

The terms "sample" and "biological sample" as used herein, refer to any sample suitable for the methods provided by the present invention. In one embodiment, the biological sample of the present invention is a tissue sample, e.g., a biopsy specimen such as samples from needle biopsy. In other embodiments, the biological sample of the present invention is a sample of bodily fluid, e.g., serum, plasma, saliva, urine, and ejaculate.

As used herein, the term "immunizing conditions" means that a peptide of the invention is contacted with a cell or administered to a subject such that it can effect its immunogenic activity. As such, the peptide, which is a T cell immunogen, generally will be administered in an immunogenic amount, typically as a priming dose followed some time later by one or more booster doses, intradermally, subcutaneously, or intramuscularly, and, if desired, formulated in a composition that includes an immunoadjuvant such as Freund's complete or incomplete adjuvant.

As used herein, the term "tolerizing conditions" means that a peptide of the invention is contacted with a cell or administered to a subject such that it induces tolerization to the otherwise immunogenic activity. As a result, a subject, for example, is tolerized to the peptide such that it is recognized as "self" by the subject and cannot effect an immune response. A peptide can be administered under tolerizing conditions by administering a tolerizing amount of the peptide, generally a small amount over a period of time, intradermally, subcutaneously, intramuscularly, or, preferably, mucosally, for example, via nasal spray or by eating.

As used herein "corresponding normal cells" means cells that are from the same organ and of the same type as the disorder or disease examined. In one aspect, the corresponding normal cells comprise a sample of cells obtained from a healthy individual. Such corresponding normal cells can, but need not be, from an individual that is age-matched and/or of the same sex as the individual providing the sample containing the cells being examined.

As used herein, the term "ameliorating" or "treating" means that the clinical signs and/or the symptoms associated with an autoimmune disorder (e.g., RA) are lessened as a result of the actions performed. The signs or symptoms to be monitored will be characteristic of the autoimmune disorder and will be well known to the skilled clinician, as will the methods for monitoring the signs and conditions. Further, the terms "reduce" and "inhibit" are used together because it is recognized that, in some cases, a decrease, for example, in the signs or symptoms associated with an autoimmune disorder can be reduced below the level of detection of a particular assay. As such, it may not always be clear whether the activity is "reduced" below a level of detection of an assay, or is completely "inhibited". Nevertheless, it will be clearly determinable, following a treatment according to the present methods, that the signs or symptoms associated with an autoimmune disorder are at least reduced from the level before treatment.

To date, three forms of antigen-independent approaches for tolerance induction have been employed for treatment of autoimmune disorders, namely, cell- and cytokine-based interventions, and stem cell therapy.

Cell-Based Biological Intervention in RA and Immune Tolerance

Immune tolerance is an active process that cannot be established by mere elimination of potentially autoreactive cells. This was underscored by the failure to treat rheumatoid arthritis (RA) by early attempts at depleting reactive T cells. Besides the potential serious side effects of such an approach, therapeutic interventions using CAMPATH and a depleting antibody against CD-4 were not successful in controlling inflammation in RA. This has lead to shift in focus into cell-based therapies that do not delete T cells, but instead potentially can modulate T cell function. Indeed, coating of the CD4 molecule instead of just depleting CD4 cells seems more beneficial than depletion.

Other avenues for modulating T cell activation include intervention at the level of T cell co-stimulation. In this context the most studied compound is a cytotoxic T-lymphocyte-associated antigen 4 (CTLA-4). For optimal T cell activation a T cell not only receives a signal through it's T cell receptor (TCR) (signal 1) but also through non-antigen specific co-stimulation, most notably CD28. CD28, constitutively expressed on T cells, interacts with CD80 and CD86 on antigen presenting cells to generate signal 2. CTLA-4 is expressed on activated T cells and binds with high affinity to CD80 and CD86 on antigen presenting cells. It thus abrogates the optimal delivery of a co-stimulatory signal through CD28 and contributes to a natural down regulation of the activated T cell. CTLA-4 can also directly inhibit T cell activation by reducing IL-2 production and IL-2 receptor expression and arresting T cells in the G1 phase of the cell cycle, while also other modes of action are suggested.

The fusion protein of the external domain of CTLA-4 with the heavy chain of human IgG1 (CTLA-4Ig) binds to CD80 and CD86 on antigen presenting cells and thus blocks the co-stimulatory signal through CD28, mimicking the natural down regulation of T cell activation. As a result autoreactive T cells can receive still signal 1, but fail to receive the co-stimulatory signal 2 through CD28 which consequently renders these cells functionally anergic. Thus, well considered regimens are as yet not adequate to use clinically.

Various animal models of autoimmune diseases have also shown clinical efficacy of CTLA4-Ig for the control of autoimmunity. Moreover, placebo control trials in RA patients receiving methotrexate showed improvement of disease activity in patients treated with CTLA4Ig. CTLA4Ig is currently also being studied in other settings in RA and for other autoimmune diseases such as SLE. Obviously, as the treatment is aimed at blocking T cell activation in general, it lacks specificity. The risks of intervention at the level of co-stimulation were very recently highlighted by the dramatic side effects in a clinical trial aimed at intervention through CD28.

Other cell-based interventions in RA include B-cell depletion. Although full-blown RA can develop even in the absence of mature B-cells, ample evidence is available for a role of B-cells and auto-antibodies in the pathogenesis of RA. Various studies have shown that indeed B-cell depletion using a chimeric anti-CD20 monoclonal antibody (rituximab) has beneficial effects in RA. Treatment with rituximab leads to an almost complete depletion of peripheral B-cells which obviously comes at the cost of an increased risk of serious infections. It seems unlikely that B-cell depletion may beneficially influence T cell tolerance, but this issue has not been addressed in studies thus far.

Cytokine Based Interventions in RA and Immune Tolerance

With regard to antigen-independent interventions, cytokine-based intervention, especially those based on the blockade of the TNF-a pathway, have been employed. TNF-a is an important mediator of inflammation and joint damage in RA. The primary clinical effect of TNF-a blockade is contributed to the direct inhibition of the effects of TNF-a and downstream cytokines. However, in RA and juvenile idiopathic arthritis so-called naturally occurring CD4+CD25+ T regulatory cells are not so much deficient in number but in regulatory function. The CD4+CD25+ regulatory cells in RA are unable to suppress the production of proinflammatory cytokines by activated T cells and monocytes. Moreover, they are incapable of inducing a regulatory phenotype in effector CD4+CD25− T cells. Following treatment with infliximab, the number of T regulatory cells in peripheral blood rises significantly. Remarkably, also the regulatory function of these previously deficient T regulatory cells is restored. These changes were especially noted in patients who responded favorably to ant-TNFa therapy, and thus suggests that the restoration of T regulatory function and immune tolerance may be a factor in the clinical efficacy of this therapy. Whether soluble TNF-a receptor, Etanercept, has a similar effects on T regulatory functions remains to be determined. It still has to be determined whether during long-term ant-TNFa therapy this state of tolerance is maintained or gradually replaced by a more pronounced immune suppression. Unfortunately, the restoration of T regulatory function under anti-TNFa therapy is insufficient because withdrawal of the treatment leads to re-occurrence of the disease within months.

Other cytokine-based interventions are being developed, including intervention through IL-1, IL-6, IL-15, IL-17 and IL-18, but their place in the treatment of RA still has to be determined.

Stem Cell Transplantation and Immune Tolerance

For about a decade autologous stem cell transplantation (ASCT) has been used as a treatment for severe refractory autoimmune disease. In arthritis, this type of treatment has especially been efficacious in juvenile idiopathic arthritis, (JIA). Remarkably, a large proportion of patients undergoing ASCT, have been in a disease free remission of their serious disease for years, even without continuous immune suppressive treatment. Thus, it would appear that following ASCT, immune tolerance is induced and maintained even long after the direct effects of the treatment are gone.

A recent study in children with JIA undergoing ASCT revealed that the restoration of immune tolerance is based on the restoration of the T regulatory compartment trough two separate mechanisms. Following ASCT a restoration of FoxP3 expressing CD4+CD25bright regulatory T cells is found, due to a preferential homeostatic expansion of CD4+CD25+ T regulatory cells during the lymphopenic phase of immune reconstitution, and to a renewed thymopoiesis of naive mRNA FoxP3 expressing CD4+CD25+ T regulatory cells. Next to the restoration of these 'natural' T regulatory cells, ASCT also induces self-heat shock protein specific T cells to deviate from a proinflammatory phenotype to a more tolerogenic phenotype, expressing IL-10 and GATA-3. These profound changes in the regulatory T cell repertoire and their apparent consequences for the clinic underline the therapeutic possibilities for tolerance induction in human autoimmune diseases. Obviously, one needs to bypass the need for far reaching therapies such as ASCT and identify different approaches that can equally effectively restore the immune balance.

Thus, in one aspect, the invention provides a method of treating a subject for an autoimmune disorder by administering a therapeutically effective amount of an immunomodulatory polypeptide. Immune pathways are affected using disease relevant polypeptides, or mimetics thereof, having immunomodulatory properties. Thus, in one embodiment, administration of the polypeptides of the invention elicits a regulatory response of the immune system in a subject by inducing changes in both the innate and adaptive arms of the immune response in a synergistic manner, particularly inducing changes in regulatory T and/or effector T cell function and repertoire towards a tolerogenic phenotype.

In another embodiment, in addition to the antigen-specific peptides, the methods include administration of a chloroquine derivative having anti-inflammatory activity. In this embodiment, administration of the chloroquine derivative provides for a nonspecific effect on reactive T cell populations by several possible mechanisms including for example a possible reduction in the processing of disease relevant peptidic motifs such that there is ultimately less processed peptide, i.e., peptide processed intracellularly, that can bind to and active effector T cell receptors. The specific mechanism of action of the chloroquine derivative is not well understood, but believed to include the induction of a change in pH within effector T cell lyposomes which change lessens or prevents processing of self peptide motifs causing in turn less disease relevant peptide from having an opportunity to be bound by T cell receptors. The outcome of such reduction in peptide processing is that circulatory T cells/receptors can be targeted with non-self peptidic motifs such as those peptides listed in Table I.

TABLE I

| Source of Heat shock peptide | Peptide Amino Acid Sequence | SEQ ID NO: |
|---|---|---|
| Human 20 (HSJ1) | KKAYRRKALQWHPDK | 1 |
| Human 23 (HDJ2) | KKAYRKLALKYHPDK | 2 |
| Human 21 (HDJ1) | KRAYRRQALRYHPDK | 3 |
| Human S2 HLA | KDLLEQKRAAVDTYC | 4 |
| Human S1 HLA | QKRAAVDTYCRHNYG | 5 |
| Ecoli dnaJ 22 | RKAYKRLAMKYHPDR | 6 |
| Ecoli mutant dnaJpV | DERAAYDQYGHAAFE | 7 |
| Ecoli dnaJP1 | QKRAAYDQYGHAAFE | 8 |
| Ecoli dnaJP 61-75 | QKRAAYDQYGHAAFEQ | 9 |
| Ecoli dnaJ 174-188 | QGFFAVQQTCPHCQG | 10 |
| Human 167 (HDJ2) | PGMVQQIQSVCMECQ | 11 |
| Ecoli dnaJ 242-256 | GDLYVQVQVKQHPIF | 12 |
| Human 280-294 | GEALSTLVLNRLKVG | 13 |

TABLE I-continued

| Source of Heat shock peptide | Peptide Amino Acid Sequence | SEQ ID NO: |
|---|---|---|
| Human 269-307 | KPLVIIAEDVDGEALSTLVLNRLKVGLQVVAVKAPGFGD | 14 |
| Ecoli 256-270 | GEALATLVVNTMRGI | 15 |
| Myc 254-268 | GEALSTLVVNKIRGT | 16 |
| Myc HSP60 243-281 | KPLLIIAEDVEGEALSTLVVNKIRGTFKSVAVKAPGFD | 17 |
| Myc 503-517 | IAGLFLTTEAVVADK | 18 |
| Myc HSP60 494-527 | KVTRSALQNAASIAGLFLTTEAVVADK PKEKA | 19 |
| Ecoli 510-524 | VAGLMITTECMVTDL | 20 |
| Human 535-546 | VASLLTTAEVVVTEI | 21 |
| Human 523-656 | KVVRTALLDAAGVASLLTTAEVVVTEIP | 22 |
| Human 256 (HDJ2) | EDLFMCMDIQLVEAL | 23 |
| Human 3 (HDJ1) | KDYYQTLGLARGASD | 24 |
| Human 5 (HDJ2) | TTYYDVLGVKPNATQ | 25 |
| Human 2 (HSJ1) | ASYYEILDVPRSASA | 26 |
| Ecoli dnaJ 4 | QDYYEILGVSKTAEE | 27 |
| Human 50 (HDJ2) | QAYEVLSDAKKRELYD | 28 |
| Human 51 (HSJ1) | EAYEVLSDKHKREIYD | 29 |
| Ecoli 212-226 | AVELESPFILLADKK | 30 |
| Ecoli 218-232 | PFILLADKKISNIRE | 31 |
| Myc 210-224 | EAVLEDPYILLVSSK | 32 |
| Myc 216-230 | PYILLVSSKVSTVKD | 33 |
| Myc 208-240 | RQEAVLEDPYILLVSSKVSTVKDLLPLLE KVIG | 34 |
| Ecoli dnaJ 209 | SKTLSVKIPGAVDTG | 35 |
| Human 242-256 | AYVLLSEKKISSIQS | 36 |
| Human 234-266 | GQKCEFQDAYVLLSEKKISSIQSIVPALEIANA | 37 |
| Human 236-250 | KCEFQDAYVLLSEKK | 38 |
| Human 410-445 | SDVEVNEKKDRVTDALNATRAAVEEGIVLGGGCALL | 39 |
| Myc 383-418 | TEVELKERKHRIEDAVRNAKAAVEEGIVAGGGVTLL | 40 |
| Ecoli dnaJ 264 | YCEVPINFAMAALGG | 41 |
| Ecoli dnaJ 268 | PINFAMAALGGEIEV | 42 |
| Human 254 (HSJ1) | DLQLAMAYSLSEMEA | 43 |
| Human 195-226 | RKGVITVKDGKTLNDELEIIEGMKFDRGISP | 44 |
| Human 469-502 | KRTLKIPAMTIAKNAGVEGSLIVEKIMQSSSE | 45 |
| Human 164 (HSJ1) | FRSVSTSTTFVQGRR | 46 |
| Human 176 (HSJ1) | GRRITTRRIMENGQE | 47 |
| Human 134 (HSJ1) | SGPFFTFSSSFPGHS | 48 |
| Human 270 (HDJ2) | LCGFQKPISTLDNRT | 49 |
| Human 197 (HSJ1) | DGQLKSVTINGVPDD | 50 |
| Human 283 (HDJ2) | RTIVITSHPGQIVKH | 51 |
| Human 318 (HDJ2) | GRLIIEFKVNFPENG | 52 |

TABLE I-continued

| Source of Heat shock peptide | Peptide Amino Acid Sequence | SEQ ID NO: |
|---|---|---|
| Human 105-127 | TNEEAGDGTTTATVLARSIAKEG | 53 |
| Myc HSP60 80-102 | TDDVAGDGTTTATVLAQALVREG | 54 |
| Myc HSP60 169-200 | NEGVITVEESNTFGLQLELTEGMRFDKGISG | 55 |
| Myc HSP60 180-188 | TFGLQLELT | 56 |
| Myc HSP60 441-478 | KVALEAPLKQIAFNSGLEPGVVAEKVRNLPAG | 57 |

As such, the methods of the invention comprise administering to the subject at least one peptide having immunomodulatory activity. Peptides having immunomodulatory activity can comprise those derived from several families of immune relevant proteins, particularly heat shock proteins. In one embodiment the peptide has the amino acid sequence of SEQ ID NO: 8. dnaJP1 (SEQ ID NO: 8) is specifically recognized in pathways that are relevant in the pathogenesis of rheumatoid arthritis. Other peptides falling within the general class of immune relevant peptides from heat shock proteins include, but are not limited to, those listed in Table I. In one embodiment, the method includes administration of an immunomodulatory peptide, such as dnaJP1, or other heat shock protein derivative, in combination with a chloroquine molecule or derivative thereof. Exemplary chloroquine molecules include, but are not limited to (hydroxyl) chloroquine, hydroxychloroquine sulfate, or a substituted chloroquine.

The peptide identified as dnaJp1 is derived from the heat shock protein (hsp) dnaJ. This peptide is a self/non-self peptide as it was derived from bacterial dnaJ but shares homology with its human equivalent. In addition, dnaJP1 contains the five amino acid cassette that is present on most of the HLA class II alleles associated with RA. In preclinical work, the most relevant epitope was mapped and its contribution to pro-inflammatory T cell responses in vitro in patients with active rheumatoid arthritis (RA) was shown. The hypothesis underlying this clinical program is that mucosal tolerization to dnaJP1 could determine an immune deviation of activated pro-inflammatory effector T cells, and that such deviation could translate into clinical benefit. Conceptually, a major difference with previous attempts at mucosal tolerization is the fact that dnaJP1 responses appear to act on amplification of autoimmune inflammation independently from its trigger and is therefore a suitable target for immune tolerization. Coincident with peptide administration, it has been shown that concomitant administration with a chloroquine derivative provides an apparent and completely unexpected and surprising synergistic effect with respect to clinical outcome.

The chloroquine derivative is a (hydroxy)chloroquine which may or may not include R' groups comprising any number of molecular structures comprising any combination of the following atoms: carbon, oxygen, hydrogen, nitrogen, chlorine, and sulfur, as are commonly known to those of ordinary skill in the art of using chloroquine derivatives for treating immune and other disorders. More specifically, the (hydroxy)chloroquine has a formula:

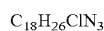

having a molecular weight of 319.877 and a structure as follows:

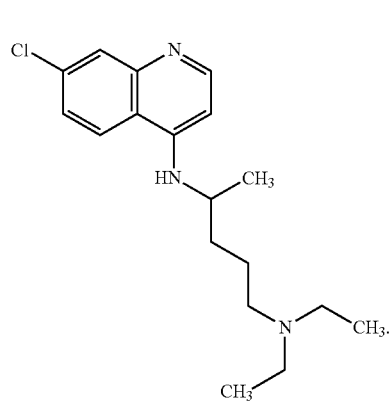 [SMILES: CCN(CC)CCCC(C)Nc1ccnc2cc(Cl)ccc12]

Alternatively, the (hydroxyl)chloroquine can further comprise a sulfate derivative having a molecular formula:

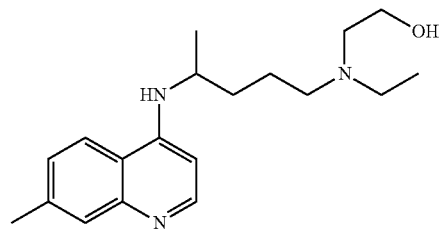 [SMILES: CCN(CCO)CCCC(C)Nc1ccnc2cc(C)ccc12]

In another embodiment, the chloroquine derivative can comprise a substituted chloroquine wherein an R' group comprising any number of chemical side groups can be attached to the core chloroquine molecule.

The chloroquine derivative (hydroxyl)chloroquine (HCQ), a DMARD, has been used for over half a century for treating malaria and certain autoimmune disorders such as RA but the mechanisms by which it achieves its effects remain uncertain. Its relative efficacy as an anti-inflammatory agent is less than other presently available antirheumatic agents. Consequently, HCQ tends to be used as an anti-inflammatory agent for patients with early RA and in patients with less aggressive disease manifestations. Because antimalarials such as HCQ are lysosomotropic, and alter the pH of lysosomes, it has been suggested that they may impact various lysosome-dependent functions in antigen presenting cells, such as assimilation and transport of MHC molecules. This in turn could have further effects, such as altering the activation of T cells. HCQ has also been shown to have direct inhibitory effects on T cells Treatment of mononuclear cells with HCQ has been shown to result in inhibition of the secretion of inflammatory cytokines. Thus, the synergistic effects of the present peptide/HCQ combination effects a variety of specific complex changes in immune driven inflammation such as is characteristic of RA.

In another embodiment the invention comprises pharmaceutical formulations comprising a combination of at least one immunomodulatory peptide of the invention and a chloroquine derivative. Alternatively, the formulations of the invention can comprise separate formulations of the immunomodulatory peptide and the chloroquine derivative intended to be administered in a combination therapy format. By "combination therapy format" is meant a therapy regimen of administering the immunomodulatory peptide and the chloroquine derivative to achieve a beneficial outcome to a patient to whom is being administered the combination of immunomodulatory peptide and the chloroquine derivative.

In recent years, molecular immunology has provided key tools for a better insight of the mechanisms which contribute to the pathogenesis of autoimmune disorders including, but not limited to, rheumatoid arthritis (RA). The chronic inflammatory nature of this disease is now better understood and many of the mediators and pathways which amplify inflammatory processes and lead to tissue damage have been identified. This progress has translated into clinical practice with the introduction of first generation of biologic agents that effectively interfere with the inflammatory cascade by blocking one of its key components, for example an inflammatory cytokine such as TNF-α.

Advances in the understanding of the regulation of the immune responses have changed our insight in basic processes that underlie autoimmune diseases. It is now well understood that recognition of self is a physiologic and necessary phenomenon. Quality and intensity of immune responses is regulated by complex mechanisms that ensure that recognition of self does not lead to damage, and that necessary inflammatory responses, aimed at clearing perceived "danger" such as an infection, are down-regulated once "danger" is eliminated. Hence, immune tolerance is the complex set of complementary and interactive pathways which contribute to the qualitative and quantitative regulation of immune responses in order to prevent tissue damage. In this context, immune tolerance involves dimming, rather than completely turning on or off a specific immune-related pathway. Coherent with this logic, autoimmunity would be defined as a situation in which these mechanisms of tolerance are impaired. Conceptually, rather than attempting to control inflammation by acting on single cytokine pathways the present invention comprises restoring physiologic modulation of inflammation via induction of immune tolerance.

In one aspect, the present invention provides methods of inducing T cell immune tolerance with the immunomodulatory peptides of the invention, depending on critical factors such as dose and route of administration and affinity and bioavailability of the antigen. T cell responses, following contact with the appropriate antigens, range from ignorance to reactivity to tolerance/anergy and such responses typically follow a U-shaped curve when comparing intensity of the response against the level of signal received by the T cell. The signal, in this context, is the sum of primary (MHC/peptide) and secondary stimuli (e.g., co-stimulatory molecules and micro-environmental factors, including for example, presence of an anti-inflammatory molecule such as for example a chloroquine derivative). With respect to the administration of immunomodulatory peptides, the quality and intensity of antigen-specific T cell responses are greatly affected by the route of administration, frequency and concentration of the antigen used. For example, excessive concentrations of an immunogen, such as a reactive peptide, may lead to lack of responses due to anergy, whilst low concentrations are not effective as the threshold of activation is not reached. The micro-environment can also influence immune outcome as the presence of a tolerogenic or a pro-inflammatory milieu strongly conditions the quality of the response of effector T cells. This effect is particular evident when the mucosal route of administration is used.

As used herein, the term "mucosal tolerance induction" refers to antigen presentation in the peculiar micro-environment of the mucosal immune system. In the context of tolerogenic stimuli, mucosal tolerance induction includes both soluble mediators, such as TGF-β and IL-10, and a "tolerogenic" phenotype of the relevant dendritic cells (DC). Thus, the ability of recognition of the antigens by specific T cells remains intact but the quality of the response changes, often inducing an immune deviation from an inflammatory to a tolerogenic type.

In human autoimmunity, antigen-specific pathogenic pathways are most certainly multiple and, thus, influencing one individual pathway may be irrelevant therapeutically. However, in the present invention, mucosal tolerization is characterizable as "infectious," insofar as regulation by antigen-specific T cells may affect effector mechanisms with a different specificity. Antigen specific mucosal tolerance has therefore the potential to affect unrelated pathogenic pathways and as such to make a therapeutic impact. *A. posteriori*, in the present invention, antigens of choice for immune tolerization are intended to reflect the antigens that participate in the modulation of inflammation in a trigger-independent fashion to achieve a better therapeutic potential. Such antigens should be readily available, and possibly over expressed at inflammatory sites. Immune responses towards such antigens, including the peptides set forth in Table I, correlate with clinical disease activity. A correlation between clinical and immunological inflammation for antigen-specific responses indicates that the antigen of choice is participating in mechanisms of modulation of immune recognition and response.

Thus, immune responses to hsp are recognized as a potent way for the immune system to react to the perception of "danger." Specifically, recognition of hsp indicates the presence of infection and the need to clear it through a potent inflammatory responses which in turn evokes mechanisms of innate immune response pathways in cooperation with more sophisticated T cell dependent epitope specific modulation. Immune responses to hsp are generated at sites where inflammation occurs and may therefore have an initially amplifying effect which needs to be modulated. The present invention provides for such modulation which leads to a progressive down-regulation of the inflammatory response in order to prevent tissue damage. The mechanisms for this regulation most likely involve T cells with regulatory function that are specific for hsp-derived antigens. This regulatory function is one component at the molecular level creating a "molecular dimmer" whose physiologic function is to modulate inflammation independently from its trigger. In autoimmunity, this modulatory function is impaired but can be restored for therapeutic purposes. Importantly, immunomodulatory peptides, such as those disclosed in Table I, provide for immune response for the requisite modulation.

In another aspect of the invention, a method for identifying an agent useful for treating an autoimmue disorder (e.g., RA) is provided. An agent useful in any of the methods of the invention can be any type of molecule, for example, a polynucleotide, a peptide, a peptidomimetic, peptoids such as vinylogous peptoids, a small organic molecule, or the like, and can act in any of various ways to ameliorate the autoimmune disorder. The agent can be administered in any way typical of an agent used to treat the particular type of autoimmune disorder, or under conditions that facilitate contact of the agent with the target cells and, if appropriate, entry into the cells. Entry of a polynucleotide agent into a cell, for example, can be facilitated by incorporating the polynucleotide into a viral vector that can infect the cells. If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell.

Candidate agents encompass numerous chemical classes, though typically they are organic molecules, preferably small organic compounds (i.e., small molecules) having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In another aspect, the methods of the invention are useful for providing a means for practicing personalized medicine, wherein treatment is tailored to a subject based on the particular characteristics of the autoimmue disorder (e.g., RA) in the subject. The method can be practiced, for example, by contacting a sample of cells from the subject with an immunomodulatory peptide of the invention in combination with a chloroquine molecule, wherein a decrease in signs and/or symptoms associated with the autoimmune disease in the presence of the immunomodulatory peptide and chloroquine molecule, as compared to the signs and/or symptoms associated with the autoimmune disease in the absence of the immunomodulatory peptide and chloroquine molecule identifies the peptide as useful for treating the disease. The sample of cells examined according to the present method can be obtained from the subject to be treated, or can be cells of an established cell line of the same type as that of the subject. In one aspect, the established cell line can be one of a panel of such cell lines, wherein the panel can include different cell lines of the same type of disease and/or different cell lines of different autoimmune disorders. Such a panel of cell lines can be useful, for example, to practice the present method when only a small number of cells can be obtained from the subject to be treated, thus providing a surrogate sample of the subject's cells, and also can be useful to include as control samples in practicing the present methods.

Once disease is established and a treatment protocol is initiated, the methods of the invention may be repeated on a regular basis to evaluate whether the level or intensity of symptoms related to the autoimmune disorder in the subject begins to approximate that which is observed in a normal subject. The results obtained from successive assays may be used to show the efficacy of treatment over a period ranging from several days to months. Accordingly, the invention is also directed to methods for monitoring a therapeutic regimen for treating a subject having an autoimmune disorder. A comparison of the level of the signs and symptoms related to the autoimmune disorder prior to and during therapy indicates the efficacy of the therapy. Therefore, one skilled in the art will be able to recognize and adjust the therapeutic approach as needed.

For administration to a subject, a peptide, or an encoding polynucleotide, generally is formulated as a composition. Accordingly, the present invention provides a composition, which generally contains, in addition to the peptide or polynucleotide of the invention, a carrier into which the peptide or polynucleotide can be conveniently formulated for administration. For example, the carrier can be an aqueous solution such as physiologically buffered saline or other solvent or vehicle such as a glycol, glycerol, an oil such as olive oil or an injectable organic esters. A carrier also can include a physiologically acceptable compound that acts, for example, to stabilize the peptide or encoding polynucleotide or to increase its absorption. Physiologically acceptable compounds include, for example, carbohydrates, such as glucose, sucrose or dextrans, antioxidants, such as ascorbic acid or glutathione, chelating agents, low molecular weight proteins or other stabilizers or excipients. Similarly, a cell that has been treated in culture for purposes of the practicing the methods of the invention, for example, synovial fluid mononuclear cells, dendritic cells, or the like, also can be formulated in a composition when the cells are to be administered to a subject.

Pharmaceutical compositions are well known in the medical arts and can include formulations in solid form such as a tablet to be administered orally. Formulations of the invention can also include liquid, gel, semisolid, colloidal, vapor and gas phase formulations capable of oral, nasal, bronchial, intestinal, or colonal (anal and perianal) delivery. In one embodiment, the compositions of the invention are administered mucosally (i.e., to the mucosa of the subject). By mucosa is meant any body mucosa including oral, nasal, bronchial, esophageal, intestinal, and anal or parianal.

It will be recognized to the skilled clinician, choice of a carrier, including a physiologically acceptable compound, depends, for example, on the manner in which the peptide or encoding polynucleotide is to be administered, as well as on the route of administration of the composition. Where the composition is administered under immunizing conditions, i.e., as a vaccine, it generally is administered intramuscularly, intradermally, or subcutaneously, but also can be administered parenterally such as intravenously, and can be administered by injection, intubation, or other such method known in the art. Where the desired modulation of the immune system is tolerization, the composition preferably is administered orally, or can be administered as above.

The term "therapeutically effective amount" or "effective amount" means the amount of a compound or pharmaceutical composition that will elicit the biological or medical response of a tissue, system, animal or human that is being sought by the researcher, veterinarian, medical doctor or other clinician. Thus, the total amount of a composition to be administered in practicing a method of the invention can be administered to a subject as a single dose, either as a bolus or by infusion over a relatively short period of time, and can be followed up with one or more booster doses over a period of time. The amount of the composition to stimulate an immune response in a subject depends on various factors including the age and general health of the subject, as well as the route of administration and the number of treatments to be administered. In view of these factors, the skilled clinician will know to adjust the particular dosage as necessary. In general, the formulation of the composition and the routes and frequency of administration are determined, initially, using Phase I and Phase II clinical trials.

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the compositions of the invention to treat an autoimmue disorder in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

Generally, treatment formulations comprising both the peptidic and chloroquine components, or formulations wherein the peptidic component is in a separate formulation from the chloroquine, can be administered in doses together, separately, in any order such that the clinical outcome is designed to affect the immune system with respect to the disease state. For example, a chronic disease state may call for a dosage regimen of each component tailored differently than a nascent disease state. Generally, a single dose of a peptide of the invention (e.g., dnaJP1) can be between 2.5 and 100 milligrams, usually between 10 and 70 mg, and even more typically between 20 and 50 mg. In one embodiment, a single dose can comprise 10, 15, 20, 25, 30, 35, 40, or even 50 mg. With respect to the chloroquine derivative, a single dose can comprise generally between 150 to 500 mg of the chloroquine derivative, usually between 190 and 450 mg, and even more typically between 200 and 400 mg. With respect to each of the immunomodulatory peptides and chloroquine derivatives, in one embodiment the peptide component is intended to be administered at least once per day, and the chloroquine component is intended to be delivered at least twice per day. In another embodiment the peptide component can be administered at least twice per day while the chloroquine component can be administered at least twice per day.

The terms "administration" or "administering" is defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The efficacy of a therapeutic method of the invention over time can be identified by an absence of symptoms or clinical signs of an immunological disorder in a subject predisposed to the disorder, but not yet exhibiting the signs or symptoms of the disorder at the time of onset of therapy. In subjects diagnosed as having the immunological disorder, or other condition in which it is desirable to modulate the immune response, the efficacy of a method of the invention can be evaluated by measuring a lessening in the severity of the signs or symptoms in the subject or by the occurrence of a surrogate end-point for the disorder. One skilled in the art will be able to recognize and adjust the therapeutic approach as needed. Accordingly, the invention is also directed to methods for monitoring a therapeutic regimen for treating a subject having an autoimmune disorder.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Combination Therapy with HCQ and dnaJP1

This example shows the efficacy of the formulations of the invention, and an administration regimen for treating rheumatoid arthritis.

A double-blinded, placebo-controlled ITT trial was designed to test for the first time if immune tolerization to dnaJp1 observed in the trial translated into clinical amelioration of the disease. dnaJP1 was tested as a first line inducer of remission in patients with early RA. A focus on capturing tolerization events over time rather than focusing on strict success determined the choice of an unconventional endpoint (AUC for time points 112, 140 and 168 days from initiation), rather than a more traditional last observation point. dnaJP1 was found to be safe and well tolerated and the rate of adverse events was similar in both the placebo and dnaJP1 groups. Table II shows the overall parameters for the study.

TABLE II

Methods phase II clinical trial with dnaJP1 in RA

| | |
|---|---|
| Study drug/comparator | Peptide dnaJP1 25 mg per os daily/placebo 25 mg per os daily |
| Eligibility criteria | >18 years old; PBMCs reactive to dnaJP1 in vitro; active RA; no significant internal disease or malignancies; disease duration <5 years; no pregnancy or nursing |
| Medication allowed | NSAIDs (stable dose), hydroxychloroquine, sulfasalazine, prednisone (<7.5 mg/day) |
| Medication prohibited (need 6 week washout) | Methotrexate, anti-TNFa agents, prednisone (>7.5 gm/day), gold, penicillamine, azathioprine, cyclophosphamide, cyclosporin |
| Setting and locations | Outpatients clinics of 11 major centers in the USA and Mexico |
| Randomization method | Permuted blocks design with a small block size, stratification by center |
| blinding | Double-blind |
| duration | 168 days + 28 days follow-up (FU) |
| Interventions | MHAQ and VAS answered by patient |
| | Joint exam for pain and swelling by physician |
| | Global assessment of disease severity by physician |
| | Recording of medication changes, compliance, adverse events |
| | Blood draw*, routine urinalysis and pregnancy test and saliva collection |
| Primary endpoint | Area under the curve (AUC) obtained by adding the response codes (0 = no response, 1 = response) for visits on days 112, 140, and 168 (individual outcome 0, 1, 2, 3) |
| Sample size | 160: 79 placebo, 81 dnajP1, based on a power of 80% and ACR20 response of 20% in placebo and 40% in dnaJP1 group at day 168 |

Summary of methods used for phase II clinical trial with dnaJP1 in RA. NSAIDS = non-steroidal anti-inflammatory drugs, MHAQ = Modified Health Assessment Questionnaire, VAS = Visual Analog Scales for pain and disease activity.
*Blood draw for rheumatoid factor, ESR and CRP, CBC with differential, ALT, creatinine, albumin and total protein and further immunological study.

(Hydroxy)chloroquine showed a synergistic interaction with dnaJP1 treatment insofar the clinical effect of dnaJP1 treatment was superior to placebo in the two groups of patients who used HCQ (placebo+HCQ n=46, dnaJP1 n=45). These two groups were homogeneous as their disease activity and other clinical and demographic characteristics were entirely comparable. There was no effect of concomitant medication on these results. Hence, epitope specific immunotherapy is hereby disclosed to have a truly enhanced effect when taken in combination with HCQ.

The mechanism of action exhibits synergism. Over all, dnaJP1 shows a sustained clinical effect that is superior to placebo. ACR outcome over time also shows this superiority. Clinical effect of dnaJP1 is highest in patients who used (hydroxy)chloroquine. Clinical outcome in dnaJP1 and placebo groups were assessed according to the American College for Rheumatology (ACR) criteria of remission. Of particular interest, clinical outcome using ACR20, ACR50 and ACR70 criteria is shown. By each of ACR20, ACR50, and ACR70 is meant that composite response-criteria that have shown to measure significant differences between placebo and test drugs and have achieved by the criteria a 20%, 50%, or 70% response to the treatment, respectively. The ACR preliminary definition of improvement in rheumatoid arthritis was applied, namely, greater or equal to a 20, 50 or 70% improvement in tender joint counts, a 20, 50 or 70% improvement in swollen joint counts and a 20, 50, or 70% improvement in 3 of the following 5 items: 1) Patient pain assessment; 2) Patient global assessment; 3) Physician global assessment; 4) Patient self-assessed functional status (using MHAQ); and 5) Acute-phase reactant (ESR or CRP). Meaningful improvement is defined as having met any of the above criteria at the end point. Patients are defined as "responders" if they meet the response criteria at any time during the study.

In each of Tables III, IV, V, and VI the following applies: Left column is day(s) after first administration, namely on day 112, 140, 168 and FU ("follow up", meaning sampling time of 1 month after the final dose day 168); second and third columns, in two patient groups each, are ACR20 responders, number of subjects and percentage of responders; and ACR50 responders, number of subjects and percentage of responders. P values for Area Under the Curve (AUC) for day 112-168 and day 112-FU are shown. The data in each Table (III, IV, V, and VI) corresponds to data shown in FIGS. 1 to 4, respectively. The data shows ACR responders in each treatment group on the different visit days throughout the study. P-values are marked for the test they are derived with: ££=Cochran-Mantel-Haenszel test (CMH) (Biochem J. April 2006, V48(2) pp 319-326), ♦=Generalized Estimating Equation Methodologies (GEE) (J. Biopharm Stat. 2005 V1 5(6) pp. 993-1007).

The treatment groups comprise: 1) All users of (hydroxy) chloroquine, placebo vs dnaJP1 (FIGS. 1A-C); 2) All patients in the study regardless of receiving, or not receiving, (hydroxyl)chloroquine (FIGS. 2A-C); 3) All non-users of (hydroxy)chloroquine, placebo vs dnaJP1 (FIGS. 3A-C); and 4) dnaJP1 alone vs placebo:(hydroxy)chloroquine alone (FIGS. 4A-C).

(Note: FIGS. 1A-C and 2A-C represent comparisons of groups who did not show differences in baseline characteristics indicating that response of combined administration of dnaJP1 and a chloroquine derivative provide surprising and unexpected synergistic results unapproachable by administration of either alone. FIGS. 4A-C however compares users of (hydroxy)chloroquine in the placebo group to non-users of (hydroxy)chloroquine in the dnaJP1 group. Since these groups were different at baseline, a direct comparison is relevant with respect to the outcome generally.

In Table III is shown results of the study with respect to patients receiving dnaJP1 and chloroquine derivative.

TABLE III

| | Patients receiving dnaJP1 and chloroquine deriviative | | | |
|---|---|---|---|---|
| | ACR 20 responders | | ACR 50 responders number (percent) | |
| | Placebo (n = 46) number (percent) | dnaJP1 (n = 45) number (percent) | Placebo (n = 46) number (percent) | dnaJP1 (n = 45) number (percent) |
| Day 112 | 16 (34.8) | 20 (44.4) | 11 (23.9) | 8 (17.8) |
| Day 140 | 12 (26.1) | 21 (46.7) | 9 (19.6) | 14 (31.1) |
| Day 168 | 9 (19.6) | 18 (40.0) | 8 (17.4) | 13 (28.9) |
| Day FU | 10 (21.7) | 22 (48.9) | 8 (17.4) | 15 (33.3) |
| AUC 112, 140, 168 | CMH p = 0.04* GEE p = 0.02* | | CMH p = 0.47 GEE p = 0.19 | |
| AUC 112, 140, 168, FU | CMH p = 0.02* GEE p = 0.002* | | CMH p = 0.27 GEE p = 0.04* | |

*represents values that are significant in that they are less than 0.05 p value

Specifically, the data in Table III show a clear dichotomy between treatment and placebo groups for ACR20 and 50 evident after day 140, a possible consequence of the time needed by the peptide and/or combination peptide and HCQ to exert an effect. The percentage ACR responders in the subgroups, herein defined as ACR20 placebo and dnaJP1, and ACR50 placebo and dnaJP1, is shown, the data reflecting placebo or dnaJP1 treatment and the concomitant use of (hydroxyl)chloroquine, on the different visit days throughout the study. P values are derived with the chi-square test.

As shown in FIG. 1A the graph indicates an unobvious, indeed unexpected and surprising, synergy between a combined predetermined dosing, of patients suffering from the effects of rheumatoid arthritis, with both dnaJP1 and (hydroxyl)chloroquine, the responders in this pivotal trial approaching 50%. As shown in FIG. 1B ACR50 criteria indicate greater than 30% response over placebo with less than 20%. FIG. 1C shows ACR70 criteria response which indicates that even for the much stricter criteria of a 70% improvement in disease status, the dnaJP1 peptide showed a meaningful result.

Data from the second group of patients, which includes all patients in the trial, are shown in Table IV.

Figure 2B:
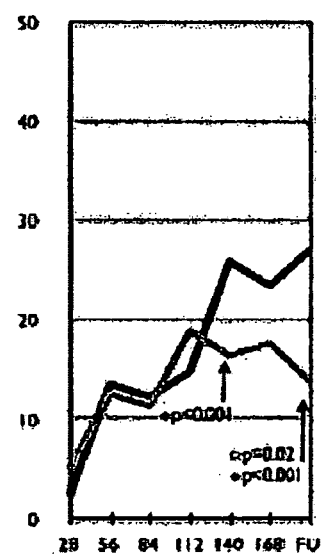
Figure 2C:
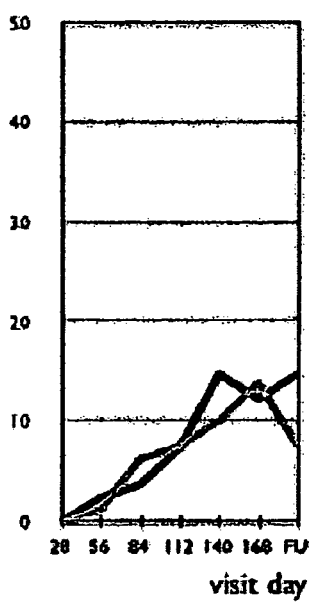

In Table IV, primary efficacy endpoint of the area under the curve (AUC) of ACR20 response rates at days 112, 140 and 168 reached a p value of 0.09 by CMH and 0.02 by GEE, which takes into account intercenter variability. ACR50 AUC was also positive by GEE (p=0.02). Post-hoc analyses were performed by considering missing data as failures. Comparing efficacy between groups at individual time points, statistical significance was found for several time points, including the last one also for ACR50. Placebo effects were unusually high for ACR50 and 70 when compared with anamnestic data in the literature. A particularly significant improvement in the signs and symptoms of RA at the follow-up visit on Day 196, indicates a lasting effect of the drug thus beneficial outcome for the patient. Even with inclusion of patients not using HCQ in the data, as significant synergy can be seen. As shown in corresponding FIGS. 2A-2C, for those patients receiving HCQ and those not receiving HCQ for each of the dnaJP1 group and the placebo group, the ACR20 response is over 40% as compared to a 20% placebo rate which appears inflated due to the presence of HCQ users in the data. It is likely that the overall response rate as shown in FIG. 2A is lower than in FIG. 1A due to the influence in the data of dnaJP1 administration alone. FIG. 2B shows ACR50 response while FIG. 2C shows ACR70 response both of which parallel the results shown in FIGS. 1A-C.

The third group comprising all non-users of (hydroxyl) chloroquine exhibited data shown in Table V.

TABLE IV

| | All Patients | | | |
|---|---|---|---|---|
| | ACR 20 responders | | ACR 50 responders number (percent) | |
| | Placebo (n = 79) number (percent) | dnaJP1 (n = 81) number (percent) | Placebo (n = 79) number (percent) | dnaJP1 (n = 81) number (percent) |
| Day 112 | 25 (31.5) | 31 (38.3) | 15 (19.0) | 12 (14.8) |
| Day 140 | 21 (26.6) | 32 (39.5) | 13 (16.5) | 21 (25.9) |
| Day 168 | 19 (24.1) | 28 (34.6) | 14 (17.7) | 19 (23.5) |
| Day FU | 17 (21.5) | 33 (40.7) | 11 (13.9) | 22 (27.2) |
| AUC 112, 140, 168 | CMHp = 0.09 GEE p = 0.02* | | CMH p = 0.44 GEE p = 0.24 | |
| AUC 112, 140, 168, FU | CMH p = 0.03* GEE p = 0.002* | | CMH p = 0.20 GEE p = 0.02* | |

*represents values that are significant in that they are less than 0.05 p value

TABLE V

| | All non-users of (hydroxyl)chloroquine | | | |
|---|---|---|---|---|
| | ACR 20 responders | | ACR 50 responders number (percent) | |
| | Placebo (n = 33) number (percent) | dnaJP1 (n = 36) number (percent) | Placebo (n = 33) number (percent) | dnaJP1 (n = 36) number (percent) |
| Day 112 | 9 (27.3) | 11 (30.6) | 4 (12.1) | 4 (11.1) |
| Day 140 | 9 (27.3) | 11 (30.6) | 4 (12.1) | 7 (19.4) |
| Day 168 | 10 (30.3) | 10 (27.8) | 6 (18.2) | 6 (16.7) |
| Day FU | 7 (21.2) | 11 (30.6) | 3 (9.1) | 7 (19.4) |
| AUC 112, 140, 168 | CMHp = 0.91 GEE p = 0.82 | | CMH p = 0.91 GEE p = 0.78 | |
| AUC 112, 140, 168, FU | CMH p = 0.84 GEE p = 0.58 | | CMH p = 0.72 GEE p = 0.51 | |

Figure 3A:
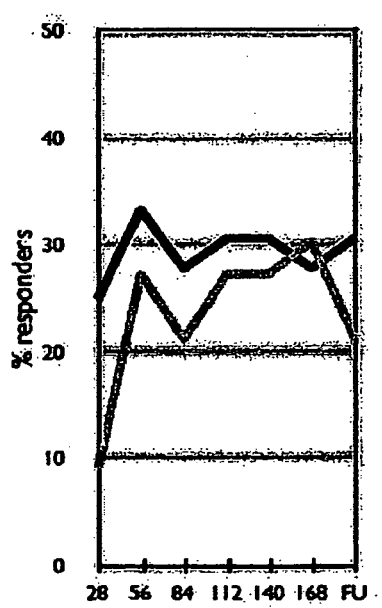
FIGS. 3A-3C show results for all patients in the study who did not receive (hydroxyl)chloroquine.
Figure 3B:
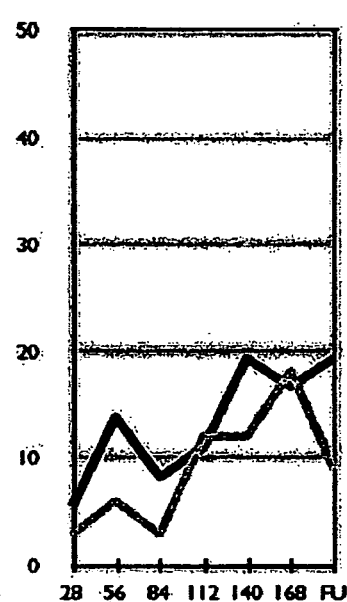
Figure 3C:
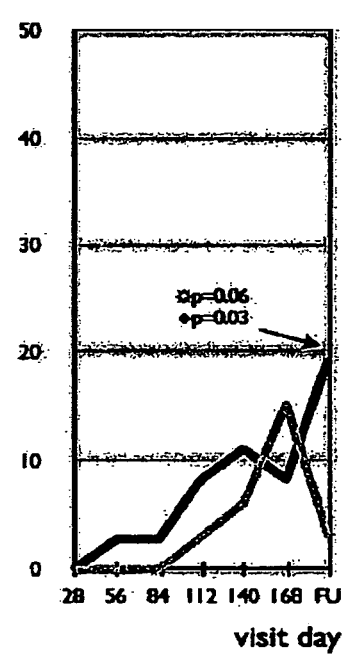

As shown in corresponding FIGS. 3A-3C, each of the dnaJP1 group and the placebo group are compared. The ACR20 response of either dnajp1 or placebo is close but dnajP1 provides an advantage. FIG. 2B shows ACR50 response while FIG. 2C shows ACR70 response.

The fourth group comprising (hydroxyl)chloroquine alone vs dnaJP1 alone exhibited data shown in Table VI.

TABLE VI

| | All patients (hydroxyl)chloroquine alone vs dnaJP1 alone | | | |
|---|---|---|---|---|
| | ACR 20 responders | | ACR 50 responders number (percent) | |
| | Placebo (n = 46) number (percent) | dnaJP1 (n = 36) number (percent) | Placebo (n = 46) number (percent) | dnaJP1 (n = 36) number (percent) |
| Day 112 | 16 (34.8) | 11 (30.6) | 11 (23.9) | 4 (11.1) |
| Day 140 | 12 (26.1) | 11 (30.6) | 9 (19.6) | 7 (19.4) |
| Day 168 | 9 (19.6) | 10 (27.8) | 8 (17.4) | 6 (16.7) |
| Day FU | 10 (21.7) | 8 (17.4) | 11 (30.6) | 7 (19.4) |
| AUC 112, 140, 168 | CMHp = 0.21 GEE p = 0.71 | CMH p = 0.53 GEE p = 0.38 | | |
| AUC 112, 140, 168, FU | CMH p = 0.14 GEE p = 0.58 | CMH p = 0.36 GEE p = 0.57 | | |

As shown in corresponding FIGS. 4A-4C, each of the dnaJP1 alone and the (hydroxyl)chloroquine alone groups are compared. The ACR20 response of dnaJP1 shows that dnajP1 provides an advantage. FIG. 4B shows ACR50 response while FIG. 4C shows ACR70 response, each indicating that anecdotally, they have an effect over time.

The set of data shown here complements the clinical and immunological results shown above. Specifically, preliminary data are provided here regarding our work on: i) characterization of immunological effects of HCQ/dnaJP1 combination therapy; ii) characterization of Treg function in RA patients treated with dnaJP1, and iii) detection of dnaJP1 specific T cells by T Cell Capture (TCC).

The clinical improvement over the coarse of treatment comprises, among other things, an accompanying decrease in the production of TNFα in response to dnaJP1 (41.8% decline) consistent with the original prediction as a secondary endpoint of a 20% decline or higher and by a corresponding increase in IL-10, with a significant negative correlation suggesting immune deviation. On the basis of these observations, it was postulated that immune deviation has occurred from an inflammatory one to one with a regulatory functional profile. Specifically, as shown in FIG. 5, the percentage of CD3+ T cells producing TNFα in response dnaJP1 decreases in the dnaJP1 treated group at day 168 significantly more than in the placebo group. (The p value in the dnaJP1 group is equal to 0.03). As further shown in FIGS. 6A and 6B, this decrease in TNFα is correlated to an increase in IL-10 in the dnaJP1 treated group (P value in the dnaJP1 group equal to 0.04).

Immunological analysis of the changes induced by treatment with dnaJP1 clearly shows a multiplicity of effects of the treatment on immune cells. This diversity is particularly evident for the HCQ/dnaJP1 combo therapy groups. This is most likely due to the synergistic effects of the two drugs. Our preliminary data, depicted below, show indeed that mechanisms of regulation based on direct cytotoxicity or release of tolerogenic cytokines may be prominent in HCQ treated patients. Two trends justify this hypothesis and are depicted below: i) production of IFN-γ and IL-10 is evidently trending upwards in patients treated with the HCQ-dnaJP1 combination. As shown in FIGS. 7A-7C and FIGS. 8A-8C, the results are expressed as the difference between day 0 and 168 in the percent of CD3+ T cells producing IFN-γ and IL-10 by T cells. The results indicate a response to stimulation with dnaJP1 higher in the group of patients treated with HCQ-dnaJP1.

This data suggests one or several of regulatory pathways involved in the observed immune deviation, which presumably relies on CD4+ class II restricted peptide specific T cells, as dnaJP1 is a class II restricted peptide. The overexpression of genes related to intracellular cytotoxic machinery suggests an additional function of dnaJP1-specific T cells in directly eliminating pathogenic T cells.

Increased expression of genes involved in the IFN-γ secretion pathway, such as CD244, and a significant increase in IFN-γ itself, provides further support for this hypothesis. This may be one of several complementary mechanisms towards controlling immune inflammation and ameliorating clinical symptoms, as seen in this study.

Figure 9A:
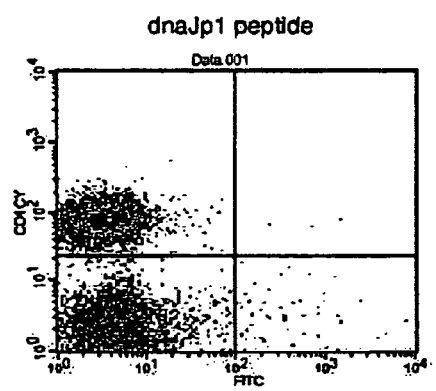
FIGS. 9A-9D are cell separation analysis showing a comparison of the number of dnaJP1-specific T cells as a percentage of total T cells before and after mucosal tolerization with dnaJP1.
Figure 9B:
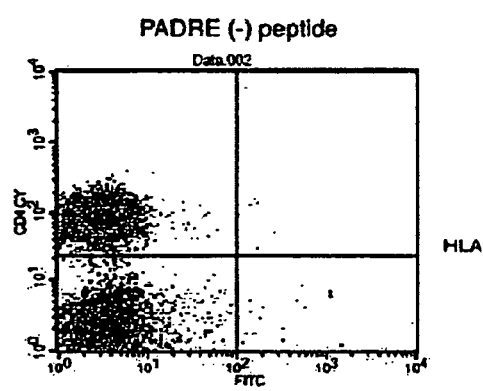
Figure 9C:
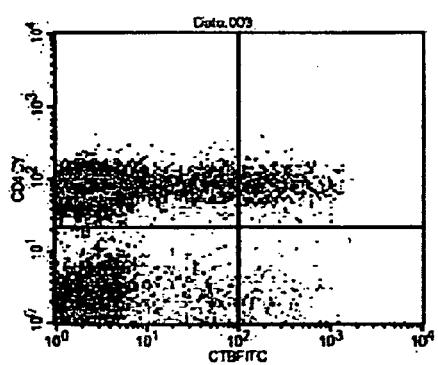
Figure 9D:
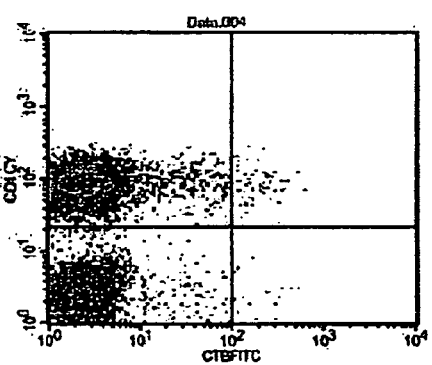

The results were further examined using T Cell Capture (TCC) to enable further characterization of dnaJP1-specific T cells. The persistence of T cell recognition of dnaJP1 in treated patients, as shown by production of regulatory cytokines upon initiation of treatment, suggested that immune deviation, rather than clonal deletion of peptide-specific T cells took place. To address this question directly dnaJP1-specific T cells were enumerated by TCC (see for example U.S. Pat. No. 7,022,483). Artificial APC (aAPC) was engineered consisting of fluorochrome-labeled aAPC incorporating HLA DRB1*0401 molecules loaded with dnaJP1 or the appropriate control peptide (PADRE−). Rafts on aAPC also contained anti CD28 and anti LFA1 antibodies. Tetramer staining was used as a comparison for characterization of CD4 dnaJP1-specific T cells measured by tetramers and TCC in a representative RA patient from the trial. PBMC from HLA-DR4 RA patient under treatment with dnaJP1 peptide were put in culture during 48 hr. with 10 µg/ml of dnaJP1 peptide. After in vitro stimulation, PBMC stained with anti CD4 (PE) antibody were incubated with Tetramers (FITC) or aAPC (FITC) loaded with a dnaJP1 or negative control peptides (PADRE−). As shown in FIGS. 9A-9D, the number of dnaJP1-specific T cells as a percentage of total T cells was compared before and after mucosal tolerization with dnaJP1. This figure compares TCC with tetramer use, another method of detecting antigen specific T cells, showing superiority of TCC. FIG. 9A shows dnaJP1 specific T cells and FIG. 9B shows background non-specific staining with a negative peptide control. Thus the teramers appear to not be efficient in staining. FIG. 9C shows the ability of TCC to detect dnaJP1-specific T cells. FIG. 9D depicts results obtained with TCC for a negative control. Thus, when comparing the total number of antigen specific T cell between time 0 and end of treatment, the number did not change significantly after treatment (before 6.50%±2.5 vs. 8.0%±2.5 after, P=0.3, n=6). These experiments demonstrated that although treatment with dnaJP1 led to a significant decrease in antigen-induced pro-inflammatory cytokine production and T cell proliferative capacities, this was not due to a loss in total number of antigen-specific T cells.

In a further examination it was observed that tolerization to dnaJP1 is associated with simultaneous production of IFN-γ and IL-10, and increased FOXP3 expression by dnaJP1-specific T cells. Several mechanisms could explain the persistence of IFN-γ producing dnaJP1-specific T cells. Most likely, different populations of dnaJP1-specific T cells are affected by the treatment. Among these, Treg cells, which produce both IFN-γ and IL-10 may be of importance. To explore this hypothesis, dnaJP1-specific T cells (identified by TCC) were sorted from selected samples (n=4) at times 0 and 7. mRNA was extracted and analyzed by Taqman for simultaneous expression of IFN-γ and IL-10. IT was found that dnaJP1-specific T cells, which produce IFN-γ and IL-10 at the same time, at the end of the treatment period (IFN-γ: 0.081±0.0054, IL-10: 0.07±0.0131/CT proband*100/CT GAPDH, n=4).

Figure 10:
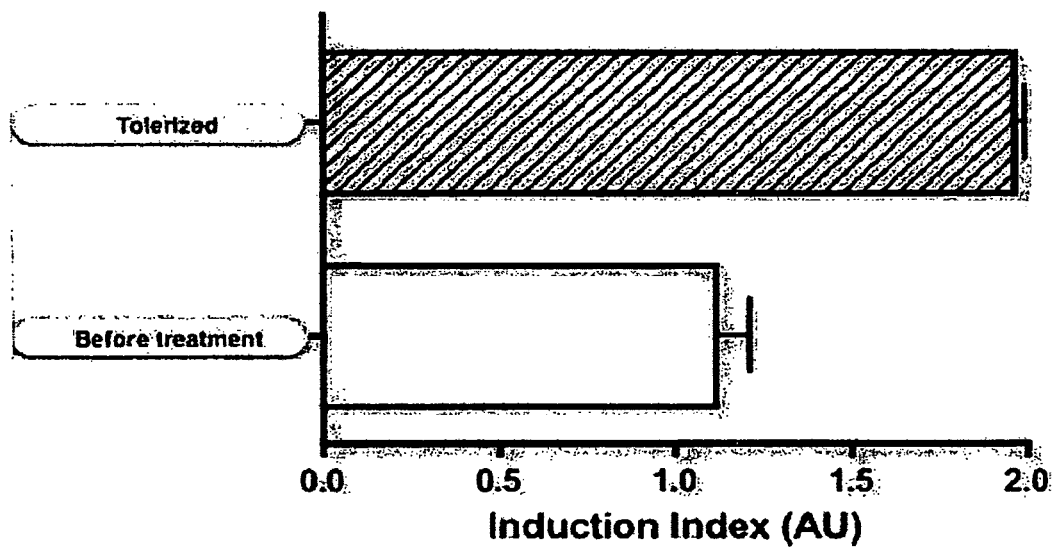
FIG. 10 is a bar graph showing immunomodulatory treatment is associated with an increase in Fox P3 expression

To further corroborate the concept that tolerization to dnaJP1 did not alter total numbers but rather function of dnaJP1 specific T cells, we studied expression of the forkhead transcription factor FOXP3. FOXP3 expression affects development and function of Treg. It is therefore been proposed as a functional marker of these regulatory cells. We tested whether tolerization to dnaJP1 would induce FOXP3 expression as an indication of restored Treg function. Samples before and after tolerization from two patients were cultured with dnaJP1. CD25+ cells were sorted and assessed for FOXP3 expression by TaqMan. FOXP3 expression by CD4+/CD25+ cells increased after tolerization. RA patients were analyzed for FOXP3 transcription factor expression. PBMC were sorted for CD4+/CD25+ cells before and after 48 hrs in vitro stimulation with dnaJP1. Total RNA was extracted and gene expression profile analyzed by TaqMan. Results are expressed as Ct values which were normalized according the expression of GAPDH. Induction index is the result of normalization process (AU) and refers how many times the gene expression compared with non stimulated. As shown in FIG. 10, Fox P3 expression increased.

One of the several advantages of our approach is its specificity and safety. In fact, the treatment exquisitely affects pro-inflammatory pathogenic pathways, leaving intact the ability of the immune system to react to challenges, such as infection. This is evidenced by the fact that, in treated patients, the ability of T cells to respond to the recall antigen Tetanus Toxoid remained intact even in the presence of a specific regulation of autoimmune inflammation. This indicates immunological safety and specificity of the treatment (not shown). Thus, as herein described, combination therapy by mucosal administration of formulations comprising a chloroquine derivative, in this example, HCQ, and/or epitope specific immunotherapy using immunogenic peptides in a regimen to dose a patient with each component either simultaneously or separately may facilitate the control of autoimmune inflammation by generating regulatory mechanisms acting on both arms of the immune system.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive. All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Although the invention has been described with reference to the above example, it will be understood that modifications and variations are encompassed within the spirit and scope of the invention. Accordingly, the invention is limited only by the following claims.

What is claimed is:

1. A composition comprising a peptide selected from the group consisting of SEQ ID NO: 1 to SEQ ID NO: 56 and SEQ ID NO: 57 and a chloroquine molecule.

2. The composition of claim 1, comprising a concentration for delivering from about 0.25 mg to 100 mg/dose of peptide and from about 150 mg to 500 mg/dose of the chloroquine molecule to the subject.

3. The composition of claim 1, wherein the chloroquine molecule is selected from the group consisting of hydroxychloroquine, hydroxychloroquine sulfate, and chloroquine.

4. The composition of claim 2, wherein the peptide is administered from about 2.5-100 mg/day in a single dose.

5. The composition of claim 2, wherein the chloroquine molecule is administered from about 200-400 mg/day in a single dose.

* * * * *

```
                              SEQUENCE LISTING

<160> NUMBER OF SEQ ID NOS: 57

<210> SEQ ID NO 1
<211> LENGTH: 15
<212> TYPE: PRT
<213> ORGANISM: Homo sapiens

<400> SEQUENCE: 1

Lys Lys Ala Tyr Arg Arg Lys Ala Leu Gln Trp His Pro Asp Lys
1               5                   10                  15

<210> SEQ ID NO 2
<211> LENGTH: 15
<212> TYPE: PRT
<213> ORGANISM: Homo sapiens

<400> SEQUENCE: 2

Lys Lys Ala Tyr Arg Lys Leu Ala Leu Lys Tyr His Pro Asp Lys
1               5                   10                  15

<210> SEQ ID NO 3
<211> LENGTH: 15
<212> TYPE: PRT
<213> ORGANISM: Homo sapiens

<400> SEQUENCE: 3

Lys Arg Ala Tyr Arg Arg Gln Ala Leu Arg Tyr His Pro Asp Lys
1               5                   10                  15

<210> SEQ ID NO 4
<211> LENGTH: 15
<212> TYPE: PRT
<213> ORGANISM: Homo sapiens

<400> SEQUENCE: 4

Lys Asp Leu Leu Glu Gln Lys Arg Ala Ala Val Asp Thr Tyr Cys
1               5                   10                  15

<210> SEQ ID NO 5
<211> LENGTH: 15
<212> TYPE: PRT
<213> ORGANISM: Homo sapiens

<400> SEQUENCE: 5

Gln Lys Arg Ala Ala Val Asp Thr Tyr Cys Arg His Asn Tyr Gly
1               5                   10                  15

<210> SEQ ID NO 6
<211> LENGTH: 15
<212> TYPE: PRT
<213> ORGANISM: Escherichia coli

<400> SEQUENCE: 6

Arg Lys Ala Tyr Lys Arg Leu Ala Met Lys Tyr His Pro Asp Arg
1               5                   10                  15
```

```
<210> SEQ ID NO 7
<211> LENGTH: 15
<212> TYPE: PRT
<213> ORGANISM: Artificial sequence
<220> FEATURE:
<223> OTHER INFORMATION: Synthetic construct: E. coli mutant

<400> SEQUENCE: 7

Asp Glu Arg Ala Ala Tyr Asp Gln Tyr Gly His Ala Ala Phe Glu
1               5                   10                  15

<210> SEQ ID NO 8
<211> LENGTH: 15
<212> TYPE: PRT
<213> ORGANISM: Escherichia coli

<400> SEQUENCE: 8

Gln Lys Arg Ala Ala Tyr Asp Gln Tyr Gly His Ala Ala Phe Glu
1               5                   10                  15

<210> SEQ ID NO 9
<211> LENGTH: 16
<212> TYPE: PRT
<213> ORGANISM: Escherichia coli

<400> SEQUENCE: 9

Gln Lys Arg Ala Ala Tyr Asp Gln Tyr Gly His Ala Ala Phe Glu Gln
1               5                   10                  15

<210> SEQ ID NO 10
<211> LENGTH: 15
<212> TYPE: PRT
<213> ORGANISM: Escherichia coli

<400> SEQUENCE: 10

Gln Gly Phe Phe Ala Val Gln Gln Thr Cys Pro His Cys Gln Gly
1               5                   10                  15

<210> SEQ ID NO 11
<211> LENGTH: 15
<212> TYPE: PRT
<213> ORGANISM: Homo sapiens

<400> SEQUENCE: 11

Pro Gly Met Val Gln Gln Ile Gln Ser Val Cys Met Glu Cys Gln
1               5                   10                  15

<210> SEQ ID NO 12
<211> LENGTH: 15
<212> TYPE: PRT
<213> ORGANISM: Escherichia coli

<400> SEQUENCE: 12

Gly Asp Leu Tyr Val Gln Val Gln Val Lys Gln His Pro Ile Phe
1               5                   10                  15

<210> SEQ ID NO 13
<211> LENGTH: 15
<212> TYPE: PRT
<213> ORGANISM: Homo sapiens

<400> SEQUENCE: 13

Gly Glu Ala Leu Ser Thr Leu Val Leu Asn Arg Leu Lys Val Gly
1               5                   10                  15
```

```
<210> SEQ ID NO 14
<211> LENGTH: 39
<212> TYPE: PRT
<213> ORGANISM: Homo sapiens

<400> SEQUENCE: 14

Lys Pro Leu Val Ile Ile Ala Glu Asp Val Asp Gly Glu Ala Leu Ser
1               5                   10                  15

Thr Leu Val Leu Asn Arg Leu Lys Val Gly Leu Gln Val Val Ala Val
            20                  25                  30

Lys Ala Pro Gly Phe Gly Asp
        35

<210> SEQ ID NO 15
<211> LENGTH: 15
<212> TYPE: PRT
<213> ORGANISM: Escherichia coli

<400> SEQUENCE: 15

Gly Glu Ala Leu Ala Thr Leu Val Val Asn Thr Met Arg Gly Ile
1               5                   10                  15

<210> SEQ ID NO 16
<211> LENGTH: 15
<212> TYPE: PRT
<213> ORGANISM: Mycobacterium mucogenicum

<400> SEQUENCE: 16

Gly Glu Ala Leu Ser Thr Leu Val Val Asn Lys Ile Arg Gly Thr
1               5                   10                  15

<210> SEQ ID NO 17
<211> LENGTH: 38
<212> TYPE: PRT
<213> ORGANISM: Mycobacterium mucogenicum

<400> SEQUENCE: 17

Lys Pro Leu Leu Ile Ile Ala Glu Asp Val Glu Gly Glu Ala Leu Ser
1               5                   10                  15

Thr Leu Val Val Asn Lys Ile Arg Gly Thr Phe Lys Ser Val Ala Val
            20                  25                  30

Lys Ala Pro Gly Phe Asp
        35

<210> SEQ ID NO 18
<211> LENGTH: 15
<212> TYPE: PRT
<213> ORGANISM: Mycobacterium mucogenicum

<400> SEQUENCE: 18

Ile Ala Gly Leu Phe Leu Thr Thr Glu Ala Val Val Ala Asp Lys
1               5                   10                  15

<210> SEQ ID NO 19
<211> LENGTH: 32
<212> TYPE: PRT
<213> ORGANISM: Mycobacterium mucogenicum

<400> SEQUENCE: 19

Lys Val Thr Arg Ser Ala Leu Gln Asn Ala Ala Ser Ile Ala Gly Leu
1               5                   10                  15

Phe Leu Thr Thr Glu Ala Val Val Ala Asp Lys Pro Lys Glu Lys Ala
            20                  25                  30
```

<210> SEQ ID NO 20
<211> LENGTH: 15
<212> TYPE: PRT
<213> ORGANISM: Escherichia coli

<400> SEQUENCE: 20

Val Ala Gly Leu Met Ile Thr Thr Glu Cys Met Val Thr Asp Leu
1               5                   10                  15

<210> SEQ ID NO 21
<211> LENGTH: 15
<212> TYPE: PRT
<213> ORGANISM: Homo sapiens

<400> SEQUENCE: 21

Val Ala Ser Leu Leu Thr Thr Ala Glu Val Val Thr Glu Ile
1               5                   10                  15

<210> SEQ ID NO 22
<211> LENGTH: 28
<212> TYPE: PRT
<213> ORGANISM: Homo sapiens

<400> SEQUENCE: 22

Lys Val Val Arg Thr Ala Leu Leu Asp Ala Ala Gly Val Ala Ser Leu
1               5                   10                  15

Leu Thr Thr Ala Glu Val Val Val Thr Glu Ile Pro
            20                  25

<210> SEQ ID NO 23
<211> LENGTH: 15
<212> TYPE: PRT
<213> ORGANISM: Homo sapiens

<400> SEQUENCE: 23

Glu Asp Leu Phe Met Cys Met Asp Ile Gln Leu Val Glu Ala Leu
1               5                   10                  15

<210> SEQ ID NO 24
<211> LENGTH: 15
<212> TYPE: PRT
<213> ORGANISM: Homo sapiens

<400> SEQUENCE: 24

Lys Asp Tyr Tyr Gln Thr Leu Gly Leu Ala Arg Gly Ala Ser Asp
1               5                   10                  15

<210> SEQ ID NO 25
<211> LENGTH: 15
<212> TYPE: PRT
<213> ORGANISM: Homo sapiens

<400> SEQUENCE: 25

Thr Thr Tyr Tyr Asp Val Leu Gly Val Lys Pro Asn Ala Thr Gln
1               5                   10                  15

<210> SEQ ID NO 26
<211> LENGTH: 15
<212> TYPE: PRT
<213> ORGANISM: Homo sapiens

<400> SEQUENCE: 26

Ala Ser Tyr Tyr Glu Ile Leu Asp Val Pro Arg Ser Ala Ser Ala

```
1               5                   10                  15
```

<210> SEQ ID NO 27
<211> LENGTH: 15
<212> TYPE: PRT
<213> ORGANISM: Escherichia coli

<400> SEQUENCE: 27

```
Gln Asp Tyr Tyr Glu Ile Leu Gly Val Ser Lys Thr Ala Glu Glu
1               5                   10                  15
```

<210> SEQ ID NO 28
<211> LENGTH: 16
<212> TYPE: PRT
<213> ORGANISM: Homo sapiens

<400> SEQUENCE: 28

```
Gln Ala Tyr Glu Val Leu Ser Asp Ala Lys Lys Arg Glu Leu Tyr Asp
1               5                   10                  15
```

<210> SEQ ID NO 29
<211> LENGTH: 16
<212> TYPE: PRT
<213> ORGANISM: Homo sapiens

<400> SEQUENCE: 29

```
Glu Ala Tyr Glu Val Leu Ser Asp Lys His Lys Arg Glu Ile Tyr Asp
1               5                   10                  15
```

<210> SEQ ID NO 30
<211> LENGTH: 15
<212> TYPE: PRT
<213> ORGANISM: Escherichia coli

<400> SEQUENCE: 30

```
Ala Val Glu Leu Glu Ser Pro Phe Ile Leu Leu Ala Asp Lys Lys
1               5                   10                  15
```

<210> SEQ ID NO 31
<211> LENGTH: 15
<212> TYPE: PRT
<213> ORGANISM: Escherichia coli

<400> SEQUENCE: 31

```
Pro Phe Ile Leu Leu Ala Asp Lys Lys Ile Ser Asn Ile Arg Glu
1               5                   10                  15
```

<210> SEQ ID NO 32
<211> LENGTH: 15
<212> TYPE: PRT
<213> ORGANISM: Mycobacterium mucogenicum

<400> SEQUENCE: 32

```
Glu Ala Val Leu Glu Asp Pro Tyr Ile Leu Leu Val Ser Ser Lys
1               5                   10                  15
```

<210> SEQ ID NO 33
<211> LENGTH: 15
<212> TYPE: PRT
<213> ORGANISM: Mycobacterium mucogenicum

<400> SEQUENCE: 33

```
Pro Tyr Ile Leu Leu Val Ser Ser Lys Val Ser Thr Val Lys Asp
1               5                   10                  15
```

<210> SEQ ID NO 34
<211> LENGTH: 33
<212> TYPE: PRT
<213> ORGANISM: Mycobacterium mucogenicum

<400> SEQUENCE: 34

Arg Gln Glu Ala Val Leu Glu Asp Pro Tyr Ile Leu Leu Val Ser Ser
1               5                   10                  15

Lys Val Ser Thr Val Lys Asp Leu Leu Pro Leu Leu Glu Lys Val Ile
            20                  25                  30

Gly

<210> SEQ ID NO 35
<211> LENGTH: 15
<212> TYPE: PRT
<213> ORGANISM: Escherichia coli

<400> SEQUENCE: 35

Ser Lys Thr Leu Ser Val Lys Ile Pro Gly Ala Val Asp Thr Gly
1               5                   10                  15

<210> SEQ ID NO 36
<211> LENGTH: 15
<212> TYPE: PRT
<213> ORGANISM: Homo sapiens

<400> SEQUENCE: 36

Ala Tyr Val Leu Leu Ser Glu Lys Lys Ile Ser Ser Ile Gln Ser
1               5                   10                  15

<210> SEQ ID NO 37
<211> LENGTH: 33
<212> TYPE: PRT
<213> ORGANISM: Homo sapiens

<400> SEQUENCE: 37

Gly Gln Lys Cys Glu Phe Gln Asp Ala Tyr Val Leu Leu Ser Glu Lys
1               5                   10                  15

Lys Ile Ser Ser Ile Gln Ser Ile Val Pro Ala Leu Glu Ile Ala Asn
            20                  25                  30

Ala

<210> SEQ ID NO 38
<211> LENGTH: 15
<212> TYPE: PRT
<213> ORGANISM: Homo sapiens

<400> SEQUENCE: 38

Lys Cys Glu Phe Gln Asp Ala Tyr Val Leu Leu Ser Glu Lys Lys
1               5                   10                  15

<210> SEQ ID NO 39
<211> LENGTH: 36
<212> TYPE: PRT
<213> ORGANISM: Homo sapiens

<400> SEQUENCE: 39

Ser Asp Val Glu Val Asn Glu Lys Lys Asp Arg Val Thr Asp Ala Leu
1               5                   10                  15

Asn Ala Thr Arg Ala Ala Val Glu Glu Gly Ile Val Leu Gly Gly Gly
            20                  25                  30

```
Cys Ala Leu Leu
        35

<210> SEQ ID NO 40
<211> LENGTH: 36
<212> TYPE: PRT
<213> ORGANISM: Mycobacterium mucogenicum

<400> SEQUENCE: 40

Thr Glu Val Glu Leu Lys Glu Arg Lys His Arg Ile Glu Asp Ala Val
1               5                   10                  15

Arg Asn Ala Lys Ala Ala Val Glu Glu Gly Ile Val Ala Gly Gly Gly
            20                  25                  30

Val Thr Leu Leu
        35

<210> SEQ ID NO 41
<211> LENGTH: 15
<212> TYPE: PRT
<213> ORGANISM: Escherichia coli

<400> SEQUENCE: 41

Tyr Cys Glu Val Pro Ile Asn Phe Ala Met Ala Ala Leu Gly Gly
1               5                   10                  15

<210> SEQ ID NO 42
<211> LENGTH: 15
<212> TYPE: PRT
<213> ORGANISM: Escherichia coli

<400> SEQUENCE: 42

Pro Ile Asn Phe Ala Met Ala Ala Leu Gly Gly Glu Ile Glu Val
1               5                   10                  15

<210> SEQ ID NO 43
<211> LENGTH: 15
<212> TYPE: PRT
<213> ORGANISM: Homo sapiens

<400> SEQUENCE: 43

Asp Leu Gln Leu Ala Met Ala Tyr Ser Leu Ser Glu Met Glu Ala
1               5                   10                  15

<210> SEQ ID NO 44
<211> LENGTH: 31
<212> TYPE: PRT
<213> ORGANISM: Homo sapiens

<400> SEQUENCE: 44

Arg Lys Gly Val Ile Thr Val Lys Asp Gly Lys Thr Leu Asn Asp Glu
1               5                   10                  15

Leu Glu Ile Ile Glu Gly Met Lys Phe Asp Arg Gly Ile Ser Pro
            20                  25                  30

<210> SEQ ID NO 45
<211> LENGTH: 32
<212> TYPE: PRT
<213> ORGANISM: Homo sapiens

<400> SEQUENCE: 45

Lys Arg Thr Leu Lys Ile Pro Ala Met Thr Ile Ala Lys Asn Ala Gly
1               5                   10                  15

Val Glu Gly Ser Leu Ile Val Glu Lys Ile Met Gln Ser Ser Ser Glu
```

-continued

```
                 20                  25                  30
```

<210> SEQ ID NO 46
<211> LENGTH: 15
<212> TYPE: PRT
<213> ORGANISM: Homo sapiens

<400> SEQUENCE: 46

```
Phe Arg Ser Val Ser Thr Ser Thr Thr Phe Val Gln Gly Arg Arg
1               5                  10                  15
```

<210> SEQ ID NO 47
<211> LENGTH: 15
<212> TYPE: PRT
<213> ORGANISM: Homo sapiens

<400> SEQUENCE: 47

```
Gly Arg Arg Ile Thr Thr Arg Arg Ile Met Glu Asn Gly Gln Glu
1               5                  10                  15
```

<210> SEQ ID NO 48
<211> LENGTH: 15
<212> TYPE: PRT
<213> ORGANISM: Homo sapiens

<400> SEQUENCE: 48

```
Ser Gly Pro Phe Phe Thr Phe Ser Ser Phe Pro Gly His Ser
1               5                  10                  15
```

<210> SEQ ID NO 49
<211> LENGTH: 15
<212> TYPE: PRT
<213> ORGANISM: Homo sapiens

<400> SEQUENCE: 49

```
Leu Cys Gly Phe Gln Lys Pro Ile Ser Thr Leu Asp Asn Arg Thr
1               5                  10                  15
```

<210> SEQ ID NO 50
<211> LENGTH: 15
<212> TYPE: PRT
<213> ORGANISM: Homo sapiens

<400> SEQUENCE: 50

```
Asp Gly Gln Leu Lys Ser Val Thr Ile Asn Gly Val Pro Asp Asp
1               5                  10                  15
```

<210> SEQ ID NO 51
<211> LENGTH: 15
<212> TYPE: PRT
<213> ORGANISM: Homo sapiens

<400> SEQUENCE: 51

```
Arg Thr Ile Val Ile Thr Ser His Pro Gly Gln Ile Val Lys His
1               5                  10                  15
```

<210> SEQ ID NO 52
<211> LENGTH: 15
<212> TYPE: PRT
<213> ORGANISM: Homo sapiens

<400> SEQUENCE: 52

```
Gly Arg Leu Ile Ile Glu Phe Lys Val Asn Phe Pro Glu Asn Gly
1               5                  10                  15
```

```
<210> SEQ ID NO 53
<211> LENGTH: 23
<212> TYPE: PRT
<213> ORGANISM: Homo sapiens

<400> SEQUENCE: 53

Thr Asn Glu Glu Ala Gly Asp Gly Thr Thr Thr Ala Thr Val Leu Ala
1               5                   10                  15

Arg Ser Ile Ala Lys Glu Gly
            20

<210> SEQ ID NO 54
<211> LENGTH: 23
<212> TYPE: PRT
<213> ORGANISM: Mycobacterium mucogenicum

<400> SEQUENCE: 54

Thr Asp Asp Val Ala Gly Asp Gly Thr Thr Thr Ala Thr Val Leu Ala
1               5                   10                  15

Gln Ala Leu Val Arg Glu Gly
            20

<210> SEQ ID NO 55
<211> LENGTH: 31
<212> TYPE: PRT
<213> ORGANISM: Mycobacterium mucogenicum

<400> SEQUENCE: 55

Asn Glu Gly Val Ile Thr Val Glu Glu Ser Asn Thr Phe Gly Leu Gln
1               5                   10                  15

Leu Glu Leu Thr Glu Gly Met Arg Phe Asp Lys Gly Ile Ser Gly
            20                  25                  30

<210> SEQ ID NO 56
<211> LENGTH: 9
<212> TYPE: PRT
<213> ORGANISM: Mycobacterium mucogenicum

<400> SEQUENCE: 56

Thr Phe Gly Leu Gln Leu Glu Leu Thr
1               5

<210> SEQ ID NO 57
<211> LENGTH: 32
<212> TYPE: PRT
<213> ORGANISM: Mycobacterium mucogenicum

<400> SEQUENCE: 57

Lys Val Ala Leu Glu Ala Pro Leu Lys Gln Ile Ala Phe Asn Ser Gly
1               5                   10                  15

Leu Glu Pro Gly Val Val Ala Glu Lys Val Arg Asn Leu Pro Ala Gly
            20                  25                  30
```